United States Patent
Veerabhadrappa et al.

(10) Patent No.: US 10,105,684 B2
(45) Date of Patent: *Oct. 23, 2018

(54) SYNTHESIS OF TRANSITION-METAL ADAMANTANE SALTS AND OXIDE NANOCOMPOSITES, AND SYSTEMS AND METHODS INCLUDING THE SALTS OR THE NANOCOMPOSITES

(71) Applicants: Saudi Arabian Oil Company, Dhahran (SA); Durham University, Durham (GB)

(72) Inventors: Manohara Gudiyor Veerabhadrappa, Durham (GB); Hugh Christopher Greenwell, Durham (GB); Gasan Selman Alabedi, Cheshire (GB); John Adrian Hall, Dhahran (SA); Andrew Whiting, Durham (GB)

(73) Assignees: Saudi Arabian Oil Company, Dhahran (SA); Durham University, Durham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/453,106

(22) Filed: Mar. 8, 2017

(65) Prior Publication Data

US 2017/0266643 A1    Sep. 21, 2017

Related U.S. Application Data

(60) Provisional application No. 62/309,653, filed on Mar. 17, 2016.

(51) Int. Cl.
*B01J 23/755* (2006.01)
*B01J 23/75* (2006.01)
(Continued)

(52) U.S. Cl.
CPC ............. *B01J 23/755* (2013.01); *B01J 21/18* (2013.01); *B01J 23/72* (2013.01); *B01J 23/75* (2013.01);
(Continued)

(58) Field of Classification Search
CPC . B01J 21/18; B01J 23/755; B01J 23/72; B01J 23/75; B01J 35/0006; B01J 37/04;
(Continued)

(56) References Cited

U.S. PATENT DOCUMENTS 3,342,880 A * 9/1967 Reinhardt ............... C07C 17/10
526/282
3,671,432 A   6/1972 Peters et al.
(Continued)

FOREIGN PATENT DOCUMENTS

CA    2594060 A1   6/2006
CN    105017485 A  11/2015
(Continued)

OTHER PUBLICATIONS

Jagadese J. Vidal, "The Chemistry of Inorganic and Organometallic Compounds with Adamantane-Like Structures." Polyhedron, vol. 15, No. 10, pp. 1585-1642 (Year: 1996).*
(Continued)

*Primary Examiner* — Patricia L. Hailey
(74) *Attorney, Agent, or Firm* — Dinsmore & Shohl LLP

(57) ABSTRACT

A method for preparing a transition-metal adamantane carboxylate salt is presented. The method includes mixing a transition-metal hydroxide and a diamondoid compound having at least one carboxylic acid moiety to form a reactant mixture, where M is a transition metal. Further, the method includes hydrothermally treating the reactant mixture at a reaction temperature for a reaction time to form the transition-metal adamantane carboxylate salt.

20 Claims, 14 Drawing Sheets

(51) Int. Cl.

| | | |
|---|---|---|
| *B01J 23/72* | (2006.01) | |
| *B01J 21/18* | (2006.01) | |
| *B01J 35/00* | (2006.01) | |
| *B01J 37/04* | (2006.01) | |
| *B01J 37/08* | (2006.01) | |
| *C07C 51/41* | (2006.01) | |

(52) U.S. Cl.
CPC .......... *B01J 35/0006* (2013.01); *B01J 37/04* (2013.01); *B01J 37/086* (2013.01); *C07C 51/412* (2013.01); *C07C 2103/74* (2013.01)

(58) Field of Classification Search
CPC .................. B01J 37/086; B01J 2523/17; B01J 2523/845; B01J 2523/847; B01J 2531/16; B01J 2531/845; B01J 2531/847; C07C 51/412; C07C 2523/72; C07C 2523/75; C07C 2523/755; C07C 2603/74
USPC .......... 502/170, 184, 185; 585/352; 568/818
See application file for complete search history.

(56) References Cited

U.S. PATENT DOCUMENTS

| | | | |
|---|---|---|---|
| 4,021,371 A | 5/1977 | Petro et al. | |
| 4,419,222 A | 12/1983 | Grenoble et al. | |
| 4,774,212 A | 9/1988 | Drezdon | |
| 4,952,748 A | 8/1990 | Alexander et al. | |
| 4,956,481 A * | 9/1990 | Gillaspey | A24B 15/345 510/104 |
| 5,021,184 A * | 6/1991 | Gillaspey | A24B 15/345 131/277 |
| 5,073,532 A | 12/1991 | Domesle et al. | |
| 5,260,495 A | 11/1993 | Forkner | |
| 5,326,891 A | 7/1994 | Breuer et al. | |
| 5,399,329 A | 3/1995 | Schutz et al. | |
| 5,635,457 A | 6/1997 | Van Slyke | |
| 5,883,041 A | 3/1999 | Pak et al. | |
| 6,096,690 A | 8/2000 | Wittenbrink et al. | |
| 6,323,270 B1 | 11/2001 | Ishida | |
| 6,410,635 B1 | 6/2002 | Kaylo et al. | |
| 6,429,314 B1 * | 8/2002 | Ishii | C07B 41/06 546/112 |
| 7,098,366 B2 | 8/2006 | Sigl et al. | |
| 7,129,287 B1 | 10/2006 | Lee et al. | |
| 7,557,063 B2 | 7/2009 | Hagemeyer et al. | |
| 7,582,202 B2 | 9/2009 | Jones et al. | |
| 7,918,935 B2 | 4/2011 | Park et al. | |
| 8,034,867 B2 | 10/2011 | Abarca et al. | |
| 8,088,349 B2 | 1/2012 | Duan et al. | |
| 8,158,843 B2 | 4/2012 | Song et al. | |
| 8,613,900 B2 | 12/2013 | Frei et al. | |
| 8,652,994 B2 | 2/2014 | Li et al. | |
| 2002/0110520 A1 | 8/2002 | Stamires et al. | |
| 2008/0108498 A1 | 5/2008 | Duan et al. | |
| 2008/0207801 A1 | 8/2008 | Ton-That et al. | |
| 2010/0279848 A1 | 11/2010 | Iyi et al. | |
| 2011/0237430 A1 | 9/2011 | Zhang et al. | |
| 2011/0248314 A1 * | 10/2011 | Takei | C08L 83/04 257/100 |
| 2012/0058739 A1 | 3/2012 | McKinzie, III et al. | |
| 2012/0258857 A1 | 10/2012 | Pham et al. | |
| 2012/0312344 A1 | 12/2012 | Delorme | |
| 2012/0322694 A1 | 12/2012 | Monteiro et al. | |
| 2013/0116351 A1 | 5/2013 | Querner et al. | |
| 2013/0143731 A1 | 6/2013 | Li et al. | |
| 2013/0172642 A1 | 7/2013 | Behrens et al. | |
| 2013/0260990 A1 | 10/2013 | Kwon et al. | |
| 2014/0113196 A1 | 4/2014 | Balaya et al. | |
| 2015/0027710 A1 | 1/2015 | Miller | |
| 2017/0029375 A1 * | 2/2017 | Harichian | C07D 215/08 |
| 2017/0266642 A1 | 9/2017 | Veerabhadrappa et al. | |
| 2017/0267620 A1 * | 9/2017 | Veerabhadrappa | B01J 31/0205 |
| 2017/0267623 A1 * | 9/2017 | Veerabhadrappa | C07C 61/135 |
| 2017/0267910 A1 | 9/2017 | Mohammed et al. | |

FOREIGN PATENT DOCUMENTS

| | | |
|---|---|---|
| EP | 1419817 A1 | 5/2004 |
| EP | 1952885 A1 | 8/2008 |
| EP | 2263976 A1 | 12/2010 |
| WO | 0224756 A2 | 3/2002 |
| WO | 2013007993 A2 | 1/2013 |
| WO | 2013072197 A1 | 5/2013 |
| WO | 2014037378 A1 | 3/2014 |
| WO | 2014052510 A1 | 4/2014 |
| WO | 2014080428 A1 | 5/2014 |

OTHER PUBLICATIONS

Abdo et al., "Clay Nanoparticles Modified Drilling Fluids for Drilling of Deep Hydrocarbon Wells", Applied Clay Science, 2013, 86, 76-82, Elsevier B.V.

Abdou et al., "Evaluation of Egyptian Bentonite and Nano-Bentonite as Drilling Mud", Egyptian Journal of Petroleum, 2013, 22, 53-59, Egyptian Petroleum Research Institute.

Alvarado et al., "Preparation and Characterization of MgO Powders Obtained from Different Magnesium Salts and the Mineral Dolomite", Polyhedron, 2000, 19, 2345-2351, Elsevier Science B.V.

Baltes et al., "Synthesis of Supported Transition Metal Oxide Catalysts by the Designed Deposition of Acetylacetonate Complexes", Langmuir, 1999, 15, 5841-5845, American Chemical Society.

Bednorz et al., "Possible High Tc Superconductivity in the Ba—La—Cu—O System", Condensed Matter, 1986, 64, 189-193, Springer-Verlag.

Bernholc et al., "Bronsted Acid Sites in Transition Metal Oxide Catalysts: Modeling of Structure, Acid Strengths, and Support Effects", J. Phys. Chem., 1987, 91, 1526-1530, American Chemical Society.

Cao et al., "Ultra-High Capacity Lithium-Ion Batteries with Hierarchical CoO Nanowire Clusters as Binder Free Electrodes", Advanced Functional Materials, 2015, 25, 1082-1089, Wiley-VCH Verlag GmbH & Co.

Cao et al., "Mg(OH)2 Complex Nanostructures with Superhydrophobicity and Flame Retardant Effects", J. Phys. Chem., 2010, 114, 17362-17368, American Chemical Society.

Choudary et al., "Benzylation of Aromatic Compounds with Different Crystallites of Mgo", Journal of American Chemical Society, 2003, 125, 2020-2021, American Chemical Society.

Di Cosimo et al., "Basic Catalysis on MgO: Generation, Characterization and Catalytic Properties of Active Sites", Catalysis, 2014, 26, 1-28.

Gardolinski et al., "Grafted Organic Derivatives of Kaolinite: I. Synthesis, Chemical and Rheological Characterization", Clay Minerals, 2005, 40, 537-546, The Mineralogical Society.

Guo et al., "A Comprehensive Review on Synthesis Methods for Transition-Metal Oxide Nanostructures", CrystEngComm, 2015, 17, 3551-3585, The Royal Society of Chemistry.

Haber, Jerzy, "Catalysis by Transition Metal Oxides", ACS Symposium Series, Washington D.C., 1985, Grasselli and Brazdil: Solid State Chemistry in Catalysis, American Chemical Society.

Hermoso et al., "Influence of Viscosity Modifier Nature and Concentration on the Viscous Flow Behaviour of Oil-Based Drilling Fluids at High Pressure", Applied Clay Science, 2014, 87, 14-21, Elsevier B.V.

Hsueh et al., "Preparation and Properties of LDHs/Epoxy Nanocomposites", Polymer, 2003, 44, 5275-5283, Elsevier Ltd.

Huang et al., "Removal of NO By Reversible Adsorption on Fe—Mn Based Transition Metal Oxides", Langmuir, 2001, 17, 4997-5003, American Chemical Society.

(56) References Cited

OTHER PUBLICATIONS

Jagadeesh et al., "Selective Oxidation of Alcohols to Esters Using Heterogeneous Co3O4—N@C Catalysts Under Mild Conditions", Journal of the American Chemical Society, 2013, 135, 10776-10782, American Chemical Society.

Jiancheng et al., "A New Type of Whole Oil-Based Drilling Fluid", Petrol. Explor. Develop., 2014, 41(4), 538-544, Elsevier B.V.

Johnson, Mark, "Spintronics", J. Phys. Chem. B, 2005, 109, 14278-14291, American Chemical Society.

Kelkar et al., "Mi-, Mg- and Co-Containing Hydrotalcite-Like Materials with a Sheet-Like Morphology: Synthesis and Characterization", Microporous Materials, 1997, 10, 163-172, Elsevier Science BV.

Krishnamoorthy et al., "Catalytic Oxidation of 1,2-Dichlorobenzene Over Supported Transition Metal Oxides", Journal of Catalysis, 2000, 193, 264-272, Academic Press.

Kumar et al., "Sonochmical Synthesis and Characterization of Nanometer-Size Transition Metal Oxides from Metal Acetates", Chem .Mater., 2000, 12, 2301-2305, American Chemical Society.

Kumar et al., "Effect of MgO Nanoparticles on Ionic Conductivity and Electrochemical Properties of Nanocomposite Polymer Electrolyte", Journal of Membrane Science, 2007, 300, 104-110, Elsevier B.V.

Lebaron et al., "Polymer-Layered Silicate Nanocomposites: An Overview", Applied Clay Science, 1999, 15, 11-29, Elsevier Science B.V.

Li et al., "Electroreduction of Carbon Monoxide to Liquid Fuel on Oxide-Derived Nanocrystalline Copper", Nature, 2014, 508, 504-507, MacMilan Publishers.

Li et al., "Mg(OH)2@reduced Graphene Oxide Composite for Removal of Dyes From Water", Journal of Materials Chemistry, 2011, 21, 13765-13768, The Royal Society of Chemistry.

Li et al., "Preparation of Nanocomposites of Metals, Metal Oxides, and Carbon Nanotubes via Self-Assembly", J. Am. Chem. Soc., 2007, 129, 9401-9409, American Chemical Society.

Li et al., "Positively Charged Nanosheets Derived via Total Delamination of Layered Double Hydroxides", Chem. Mater., 2005, 17, 4386-4391, American Chemical Society.

Li et al., "Stable Platinum Nanoparticles on Specific MgAl2O4 Spinal Facets at High Temperatures in Oxidizing Atmospheres", Nature Communications, 2013, DOI: 10.1038/ncomms3481, MacMilan Publishers Limited.

Liu et al., "Layered Double Hydroxide Nano- and Microstructures Grown DIrectly on Metal Substrates and Their Calcined Products for Application as Li-Ion Battery Electrodes", Advanced Functional Materials, 2008, 18, 1448-1458, Wiley-VCH Verlag GmbH & Co.

Liu et al., "Gold-Catalyzed Direct Hydrogenative Coupling of Nitroarenes to Synthesize Aromatic Azo Compounds", Angew. Chem., 2014, 126, 7754-7758, Wiley-VCH Verlag GmbH & Co.

Liu et al., "Selective and Controlled Synthesis of a- and b- Cobalt Hydroxides in Highly Developed Hexagonal Platelets", J. Am. Chem. Soc., 2005, 127, 13869-13874, American Chemical Society.

Ma et al., "Metal-Organic Framework Derived Hybrd Co3O4-Carbon Porous Nanowire Arrays as Reversible Oxygen Evolution Electrodes", J. Am. Chem. Soc., 2014, 136, 13925-13931, American Chemical Society.

Makhluf et al., "Microwave-Assisted Synthesis of Nanocrystalline MgO and Its Use as a Bacteriocide", Adv. Funct. Mater., 2005, 15, 1708-1715, Wiley-VCH Verlag GmbH.

Mishra et al., "Effect of Nano-Mg(OH)2 on the Mechanical and Flame-Retarding Properties of Polypropylene Composites", Journal of Applied Polymer Science, 2004, 94, 116-122, Wiley Periodicals, Inc.

Nethravathi et al., "Synthesis and Anion-Exchange Reactions of a New Anionic Clay a-Magnesium Hydroxide", Journal of Colloid and Interface Science, 2011, 354, 793-797, Elsevier Inc.

Newman et al., "Comparative Study of Some Layered Hydroxide Salts Containing Exchangeable Interlayer Anions", Journal of Solid State Chemistry, 1999, 148, 26-40, Academic Press.

Nielsen et al., "Delamination, Synthesis, Crystal Structure and Thermal Properties of the Layered Metal-Organic Compound Zn(C12H14O4)", J. Mater. Chem., 2008, 18, 1002-1007, The Royal Society of Chemistry.

Ning et al., "Gas-Hydrate Formation, Agglomeration and Inhibition in Oil-Based Drilling Fluids for Deep-Water Drilling", Journal of Natural Gas Chemistry, 2010, 19, 234-240, Elsevier.

Oswald et al., "Bivalent Metal Hydroxides", Preparation and Crystal Growth of Materials with Layered Structures, 1977, 71-140.

Park et al., "Synthesis and Characterization of Al(OH)3/Polystyrene Nanocomposite Latex Particles by Emulsion Polymerization", Macromol. Symp., 2007, 247-250.

Pham et al., "A Silica-Supported Iron Oxide Catalyst Capable of Activating Hydrogen Peroxide at Neutral pH Values", Environ. Sci. Technol., 2009, 43, 8930-8935, American Chemical Society.

Pupovac et al. "Cu/MgAl2O4 as Bifunctional Catalyst for Aldol Condensation of 5-Hydroxymethylfurfural and Selective Transfer Hydrogenation", ChemSusChem, 2013, 6, 2103-2110.

Qian et al., "Micropore Modification of Zeolites with Transition-Metal Oxides", Colloids and Surfaces A: Physiochemical and Engineering Aspects, 2001, 180, 311-316, Elsevier Science B.V.

Rajamathi et al., "The Many Ways of Making Anionic Clays", Proc. Indian Acad. Sci. (Chem. Sci.), 2001, 5 & 6, 671-680, Indian Academy of Sciences.

Ramirez, A.P., "Colassal Magnetoresistance", J. Phys.: Condens. Matter, 1997, 9, 8171-8199, IOP Publishing Ltd.

Rao et al., "Synthesis of Complex Metal Oxides by Novel Routes", Acc. Chem. Res., 1987, 20, 228-235, American Chemical Society.

Rao, C.N.R., "Transition Metal Oxides", Annu. Rev. Phys. Chem., 1989, 40, 291-326, Annual Reviews Inc.

Raveau, B., "Transition Metal Oxides: Promising Functional Materials", Journal of the European Ceramic Society, 2005, 25, 1965-1969, Elsevier Ltd.

Reddy et al., "Metal Oxides and Oxysalts as Anode Materials for Li Ion Batteries", Chem. Rev. 2013, 113, 5364-5457, American Chemical Society.

Moorhead-Rosenberg et al., "A Rapid Microwave-Assisted Solvothermal Approach to Lower-Valent Transition Metal Oxides", Inorg. Chem., 2013, 52, 13087-13093, American Chemical Society.

Schwertfeger et al., "Diamonds are a Chemist's Best Friend: Diamondoid Chemistry Beyond Adamantane", Angew. Chem. Int. Ed., 2008, 47, 1022-1036, Wiley-VCH GmbH & Co.

Schwertmann et al., "The Formation of Green Rust and Its Transformation to Lepidocrocite", Clay Minerals, 1994, 29, 87-92, The Mineralogical Society.

Singoredjo et al., "Alumina Supported Manganese Oxides for the Low-Temperature Selective Catalytic Reduction of Nitric Oxide with Ammonia", Applied Catalysis B: Environmental, 1992, 1, 297-316, Elsevier Science Publishers B.V.

Spaldin et al., "The Renaissance of Magnetoelectric Multiferroics", Science, 2005, 309, 391-392, AAAS.

Spyrou et al., "Towards Novel Multifunctional Pillared Nanostructures: Effective Intercalation of Adamantylamine in Graphene Oxide and Smectite Clays", Adv. Funct. Mater., 2014, 24, 2841-5850, Wiley-VCH Verlag GmbH & Co.

Stankic et al., "Size-Dependent Optical Properties of MgO Nanocubes", Angew. Chem. Int. Ed., 2005, 44, 4917-4920, Wiley-VCH Verlag GmbH & Co.

Stein et al., "Salt-Gel Synthesis of Porous Transition-Metal Oxides", Chem. Mater., 1995, 7, 304-313, American Chemical Society.

Tao et al., "Synthesis and Characterization of Layered Double Hydroxides with a High Aspect Ratio", Journal of Solid State Chemistry, 2006, 179, 708-715, Elsevier Inc.

Tian et al., "Manganese Oxide Mesoporous Structures: Mixed-Valent Semiconducting Catalysts", Science, 1997, 276, 926-930.

Tokura et al., "Orbital Physics in Transition-Metal Oxides", Science, 2000, 288, 462-468.

Vidal-Michel et al., "Effect of Crystal Size on the Oxidative Dehydrogenation of Butane on V/MgO Catalysts", Journal of Catalysis, 2004, 221, 127-136, Elsevier Inc.

Walia et al., "Transition Metal Oxides—Thermoelectric Properties", Progress in Materials Science, 2013, 58, 1443-1489, Elsevier Ltd.

(56) References Cited

OTHER PUBLICATIONS

Wang et al., "Electronics and Optoelectronics of Two-Dimensional Transition Metal Dichalcogenides", Nature Nanotechnology, 2012, 7, 699-712, Macmilan Publishers.

Wang et al., "CO2 Capture by Solid Adsorbents and Their Applications: Current Status and New Trends", Energy Environ. Sci., 2011, 4, 42-55, The Royal Society of Chemistry.

Westerhaus et al., "Heterogenized Cobalt Oxide Catalysts for Nitroarene Reduction by Pyrolysis of Molecularly Defined Complexes", Nature Chemistry, 2013, 5, 537-543.

Xie et al., "Low-Temperature Oxidation of Co Catalysed by Co3O4 Nanorods", Nature, 2009, 458, 746-749, Macmilian Publishers Limited.

Xu et al., "Surface Area and Thermal Stability Effect of the MgO Supported Catalysts for the Synthesis of Carbon Nanotubes", Journal of Materials Chemistry, 2008, 18, 5738-5745, The Royal Society of Chemistry.

Zhang et al., "Synthesis and Transformation of Linear Adamantane Assemblies Inside Carbon Nanotubes", ACS Nano, 6:10, 8674-8683.

Zhang et al., "Hydrogen Production via the Direct Cracking of Methane Over Silica-Supported Nickel Catalysts", Applied Catalysts A: General, 1998, 167, 161-172, Elsevier B.V.

Zhuang et al., "Comparative Study on the use of Cationic-Nonionic-Organo-Montmorillonite in Oil-Based Drilling Fluids", Applied Clay Science, 2015, 116-117, 257-262, Elsevier B.V.

International Search Report and Written Opinion pertaining to PCT/US2017/021135 dated Jun. 12, 2017.

International Search Report and Written Opinion pertaining to PCT/US2017/022427 dated Jun. 12, 2017.

International Search Report and Written Opinion pertaining to PCT/US2017/021478 dated May 29, 2017.

Lu et al., "Sheet-like and Fusiform CuO Nanostructures Grown on Graphene by Rapid Microwave Heating for High Li-Ion Storage Capacities", J. Mater. Chem., 2011, 21, 17916.

Huang et al., "Controllable Preparation of Nano-MgO and Investigation of its Bactericidal Properties", Journal of Inorganic Biochemistry, 2005, 99, 986-996.

International Search Report dated Jul. 13, 2017, pertaining to PCT/US2017/022485, filed Mar. 15, 2017, 7 pages.

Written Opinion dated Jul. 13, 2017, pertaining to PCT/US2017/022485, filed Mar. 15, 2017, 11 pages.

Cavani et al., Hydrotalcite-Type Anionic Clays: Preparation, Properties and Applications, Catalysis Today, vol. 11, 1991, 173-301, Elsevier Science Publishers B.V.

Chang, et al., "Ca-Rich Ca—Al-Oxide, High-Temperature-Stable Sorbents Prepared from Hydrotalcite Precursors: Synthesis, Characterization, and CO2 Capture Capacity", ChemSusChem, 2011, vol. 4, 1844-1851, Wiley-VCH.

Chen, et al., "Preparation and Characterization of Flexible Asymmetric Supercapacitors Based on Transition-Metal-Oxide Nanowire/Single-Walled Carbon Nanotube Hybrid Thin-Film Electrodes", ACSNano, 2010, vol. 4, No. 8, 4403-4411, American Chemical Society.

Damodara et al., "Copper Nanoparticles from Copper Aluminum Hydrotalcite: An Efficient Catalyst for Acceptor- and Oxidant-Free Dehydrogenation of Amines and Alcohols", Adv. Synth. Catal., 2014, vol. 356, 189-198, Wiley-VCH.

Del Arco et al., "Release studies of different NSAIDS encapsulated in Mg, Al, Fe-hydrotalcites" Applied Clay Science, vol. 42, 2009, 538-544, Elsevier B.V.

Ding, et al., "Equilibria and kinetics of CO2 absorption on hydrotalcite adsorbent" Chemical Engineering Science, 2000, vol. 55, 3461-3474, Elsevier Science Ltd.

Gardolinski et al., "Grafted organic derivatives of kaolinite: II. Intercalation of primary n-alkylamines and delamination", Clay Minerals, 2005, vol. 40, 547-556, The Mineralogical Society.

Itoh, et al., Nanoscale Metal Oxide Particles as Chemical Reagents. Intrinsic Effects of Particle Size on Hydroxyl Content and on Reactivity and Acid/Base Properties of Ultrafine Magnesium Oxide, Chem. Mater. 1993, vol. 5, 71-77, American Chemical Society.

Khan, et al., "Intercalation chemistry of layered double hydroxides: recent developments and applications", Journal of Materials Chemistry, 2002, vol. 12, 3191-3198, The Royal Society of Chemistry.

Kumar, et al., "Sonochemical Synthesis and Characterization of Nanometer-Size Transition Metal Oxides from Metal Acetates" Chem. Mater. 2000, vol. 12, 2301-2405, American Chemical Society.

Kumbhar, et al., Reduction of Aromatic Nitro Compounds with Hydrazine Hydrate in the Presence of the Iron(III) Oxide-MgO Catalyst Prepared from a Mg—Fe Hydrotalcite Prescursor, Tetrahedron Letters, 1998, vol. 39, 2573-2574, Elsevier Science Ltd.

Kumbhar, et al., Mg—Fe Hydrotalcite as a Catalyst for the Reduction of Aromatic Nitro Compounds with Hydrazine Hydrate, Journal of Catalysis, 2000, vol. 191, 467-473, Academic Press.

Li et al., "Mg(OH)2@reduced graphene oxide composite for removal of dyes from water", Journal of Materials Chemistry, 2011, vol. 21, 13765-13768, The Royal Society of Chemistry.

Meyn et al., "Anion-Exchange Reactions of Layered Double Hydroxides" Inorg. Chem. 1990, vol. 29, 5201-5207, American Chemical Society.

Miyata, Shigeo, "Physico-Chemical Properties of Synthetic Hydrotalcites in Relation to Composition", Clays and Clay Minerals, 1980, vol. 28, No. 1, 50-56, The Clay Minerals Society.

Mulukutla, C. Detellier, "Thermally activated Mg, Fe layered double hydroxide as reductant for nitric oxide, Journal of Materials Science Letters" 1996, vol. 15, 797-799, Chapman & Hall.

Nethrvathi, et al., Cobalt Hydroxide/Oxide Hexagonal Ring-Graphene Hybrids through Chemical Etching of Metal Hydroxide Platelets by Graphene Oxide: Energy Storage Applications, ASCNano, 2014, vol. 8, No. 3, 2755-2765, American Chemical Society.

Poizot et al., Nano-sized transition-metal oxides as negative-electrode materials for lithium-ion batteries, Nature, 2000, vol. 407, pp. 496-499, Macmillan Magazines Ltd.

Prasanna, et al., Chromate uptake characteristics of pristine layered double hydroxides of Mg with Al, Solid State Sciences, 2008, vol. 10, 260-266, Elsevier Masson SAS.

Reichle, Walter T., "Catalytic Reactions by Thermally Activated Anionic Clay Minerals" Journal of Catalysis, 1985, vol. 94, 547-557, Academic Press, Inc.

Shukla, et al., "Stabilized a-Ni(OH)2 as Electrode Material for Alkaline Secondary Cells", J. Electrochem Soc., 1994, vol. 141, No. 11, 2956-2959, The Electrochemical Society, Inc.

Tao et al., "A redox-stable efficient anode for solid-oxide fuel cells" Nature Materials, 2003, vol. 2, 320-323, Nature Publishing Group.

Wang, et al., "Synthesis of high-temperature CO2 adsorbents from organo-layered double hydroxides with markedly improved CO2 capture capacity" The Royal Society of Chemistry, 2012, vol. 5, 7526-7530, Energy Environ. Sci.

White et al., Supported metal nanoparticles on porous materials. Methods and Applications; The Royal Society of Chemistry 2009, vol. 38, 481-494, Chemical Society Reviews.

Williams, et al., "Towards understanding, control and application of layered double hydroxide chemistry", Journal of Materials Chemistry, 2006, vol. 16, 3065-3074, Journal of Materials Chemistry.

Yao, et al., "Confined adamantane molecules assembled to one dimension in carbon nanontubes" Carbon, 2011, vol. 49, 1159-1166, Elsevier Ltd.

Yavuz, et al., "Markedly Improved CO2 Capture Efficiency and Stability of Gallium Substituted Hydrotalcites at Elevated Temperatures" Chem. Mater. 2009, vol. 21, 3473-3475, American Chemical Society.

Zhao, et al., "Carbon Nanowire Made of a Long Lineal Carbon Chain Inserted Inside a Multiwalled Carbon Nanotube", Physical Review Letters, 2003, vol. 90, No. 18, 187401-1-187401-4, The American Physical Society.

International Search Report dated Jul. 13, 2017, pertaining to PCT/US2017/021550, filed Mar. 9, 2017, 8 pages.

(56) References Cited

OTHER PUBLICATIONS

Written Opinion dated Jul. 13, 2017, pertaining to PCT/US2017/021550, filed Mar. 9, 2017, 13 pages.

J. Costantino, et al., Preparation and characterization of hydrotalcite/carboxyadamantane intercalation compounds as fillers of polymeric nanocomposites, Journal of Materials Chemistry, vol. 17, No. 11, Dec. 22, 2006, pp. 1079-1086.

Goh, et al., Application of layered double hydroxides for removal of oxyanions: A review, Water Research, Elsevier, vol. 42, No. 6-7, Nov. 7, 2007, pp. 1343-1368, Amsterdam, Netherlands.

Kanezaki, Unexchangeable Interlayer Anions: Synthesis and Characterization of Zn/Al- and Mg/A1-Layered Double Hydroxides with Interlayer Alizarin red S, Journal of Inclusion Phenomena and Macrocyclic Chemistry, Jun. 1, 2003, pp. 89-95, https://rd.springer.com.

Crepaldi, et al., Sorpotion of terephthalate anions by calcined and uncalcined hydrotalcite-like compounds, Colloids and Surfaces A: Physicochem. Eng. Aspects 211, vol. 211, No. 2-3, Jun. 4, 2002, pp. 103-114, Amsterdam, Netherlands.

Sabbar, et al., Probing the interaction between di- and tri-functionalized carboxy-phosphonic acid and LDH layer structure, Journal of Physics and Chemistry of Solids, Pergamon Press, vol. 67, No. 11, Sep. 6, 2006, pp. 2419-2429, London, England.

Lima, et al., Characterization of basic catalysts by the use of nitromethane as NMR probe molecule and reactant, Journal of Cataly, Academic Press, vol. 223, No. 1, Feb. 20, 2004, pp. 28-35, USA.

Khan, et al, The intercalation of bicyclic and tricyclic carboxylates into layered double hydroxides, Journal of Solid State Chemistry, vol. 183, No. 12, Sep. 30, 2010, pp. 2877-2885, USA.

Chen et al., "Cu2(ATC) 6H2O: Design of Open Metal Sites in Porous Metal-Organic Crystals (ATC: 1,3,5,70Adamantane Tetracarboxylate", J. Am. Chem. Soc., 2000, 122, 11559-11560.

Kim et al., "Assembly of Metal-Organic Frameworks from Large Organic and Inorganic Secondary Building Units: New Examples and Simplifying Principles for Complex Structures", J. Am. Chem. Soc., 2001, 123, 8239-8247.

Non-Final Office Action dated Jan. 5, 2018 pertaining to U.S. Appl. No. 15/453,180, filed Mar. 8, 2017.

Vittal, The Chemistry of Inorganic and Organometallic Compounds with Adamantane-Like Structures: Polyhedron, vol. 15, No. 10, pp. 1585-1642 (1996).

Non-Final Office Action dated Apr. 23, 2018 pertaining to U.S. Appl. No. 15/449,347, filed Mar. 3, 2017.

U.S. Non-Final Office Action dated May 25, 2018, pertaining to U.S. Appl. No. 15/449,207.

International Search Report and Written Opinion dated Aug. 10, 2018 pertaining to International Application No. PCT/US2018/030399, 15 pages.

U. Costantino et al., Preparation and characterisation of hydrotalcite/carboxyadamantane intercalation compounds as fillers of polymeric nanocomposites, Journal of Materials Chemistry, 2007, vol. 17, pp. 1076-1086, www.rsc.org/materials, UK.

Makoto Ogawa, et al., Hydrothermal Synthesis of Layered Double Hydroxide-Deoxycholate Intercalation Compounds, Chemical Materials, 2000, vol. 12, pp. 3253-3255, USA.

\* cited by examiner

SYNTHESIS OF TRANSITION-METAL ADAMANTANE SALTS AND OXIDE NANOCOMPOSITES, AND SYSTEMS AND METHODS INCLUDING THE SALTS OR THE NANOCOMPOSITES

CROSS-REFERENCE TO RELATED APPLICATIONS

This application claims the benefit of U.S. Provisional Application Ser. No. 62/309,653 filed Mar. 17, 2016, incorporated herein by reference.

BACKGROUND

Field

The present specification generally relates to transition-metal diamondoid salts, nanocomposites containing transition-metal oxides derived from the salts, to systems and methods including the salts or the nanocomposites, and to polymer composites including the salts or the nanocomposites.

Abbreviations

° C.=Degrees Celsius
Å=Angstroms
ACA=1-adamantane carboxylic acid
AC=adamantane carboxylate
cm=centimeter ($10^{-2}$ meter)
Co(x)-AC=cobalt adamantane carboxylate prepared from reactant mixture having $Co^{2+}$ to ACA molar ratio of x:1
Co-AC=cobalt adamantane carboxylate
Cu(x)-AC=copper adamantane carboxylate prepared from reactant mixture having $Cu^{2+}$ to ACA molar ratio of x:1
Cu-AC=copper adamantane carboxylate
EDX=Energy-dispersive X-ray
h=hours
HRTEM=High-resolution transmission electron microscopy
IR=Infrared
LDH=layered double hydroxide
μm=micrometer ($10^{-6}$ meter)
Ni(x)-AC=nickel adamantane carboxylate prepared from reactant mixture having $Ni^{2+}$ to ACA molar ratio of x:1
Ni-AC=nickel adamantane carboxylate
nm=nanometer ($10^{-9}$ meter)
PXRD=Powder X-ray diffraction
SEM=Scanning electron microscopy
TEM=Transmission electron microscopy
TGA=Thermogravimetric analysis
TMO=Transition metal oxide
wt. %=Weight percent

TECHNICAL BACKGROUND

Transition metal oxides (TMOs) are a widely studied class of oxides having varied electronic, optical, magnetic, chemical and mechanical properties. Generally, TMOs are prepared by solid state synthesis methods at high temperatures. High-temperature solid state synthesis can be cumbersome, particularly with regard to controlling the size and shape of the resultant TMOs, and often can result in impurities arising from the diffusion length barriers of the reactants. Accordingly, significant need exists for synthetic methods that provide TMO materials and composites of TMO materials that are stable or dispersible and that enable control of size and shape of the TMO materials. Further ongoing needs exist for systems, methods, and composite materials that include the TMO materials.

SUMMARY

According some embodiments, a method for preparing a transition-metal adamantane carboxylate salt is provided. The method includes mixing a transition-metal hydroxide and a diamondoid compound having at least one carboxylic acid moiety to form a reactant mixture, where M is a transition metal and hydrothermally treating the reactant mixture at a reaction temperature for a reaction time to form the transition-metal adamantane carboxylate salt.

According to further embodiments, a method for preparing a nanocomposite is provided. The method includes thermally decomposing a transition-metal adamantane carboxylate salt to form the nanocomposite.

According to further embodiments, a catalyst system is provided. The catalyst system includes a transition-metal adamantane carboxylate salt, a nanocomposite formed by thermally decomposing a transition-metal adamantane carboxylate salt, or a mixture of a transition-metal adamantane carboxylate salt and a nanocomposite formed by thermally decomposing a transition-metal adamantane carboxylate salt.

According to further embodiments, a method for catalyzing a chemical reaction between at least one first reactant and at least one second reactant is provided. The method includes reacting the at least one first reactant and at least one second reactant in the presence of a catalyst system which includes a transition-metal adamantane carboxylate salt, a nanocomposite formed by thermally decomposing a transition-metal adamantane carboxylate salt, or a mixture of a transition-metal adamantane carboxylate salt and a nanocomposite formed by thermally decomposing a transition-metal adamantane carboxylate salt.

According to further embodiments, a method for catalyzing the decomposition of a reactant is provided. The method includes decomposing the reactant in the presence of a catalyst system which includes a transition-metal adamantane carboxylate salt, a nanocomposite formed by thermally decomposing a transition-metal adamantane carboxylate salt, or a mixture of a transition-metal adamantane carboxylate salt and a nanocomposite formed by thermally decomposing a transition-metal adamantane carboxylate salt.

According to further embodiments, a polymer composite is provided. The polymer composite includes at least one polymer or copolymer; and at least one filler material interspersed among the at least one polymer or copolymer to form a composite. The at least one filler material is chosen from: (a) a transition-metal adamantane carboxylate salt prepared according to embodiments of this disclosure; (b) a nanocomposite prepared according to embodiments of this disclosure; or (c) a mixture of (a) and (b).

According to further embodiments, a system for removing a chemical compound from a fluid stream is provided. The system includes an adsorbent chosen from: (a) a transition-metal adamantane carboxylate salt prepared according to embodiments of this disclosure; (b) a nanocomposite prepared according to embodiments of this disclosure; or (c) a mixture of (a) and (b). The system also includes a vessel in which or on which the chemical compound in the fluid stream is contacted with the adsorbent.

According to yet further embodiments, a drilling fluid is provided. The drilling fluid includes at least one rheology modifier chosen from: (a) a transition-metal adamantine carboxylate salt prepared according to embodiments of this disclosure; (b) a nanocomposite prepared according to embodiments of this disclosure; or (c) a mixture of (a) and (b).

Additional features and advantages of the embodiments described in this specification will be set forth in the detailed description which follows, and in part will be readily apparent to those skilled in the art from that description or recognized by practicing the embodiments described in this specification, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described in this specification, and together with the description serve to explain the principles and operations of the claimed subject matter.

DETAILED DESCRIPTION

Figure 1:
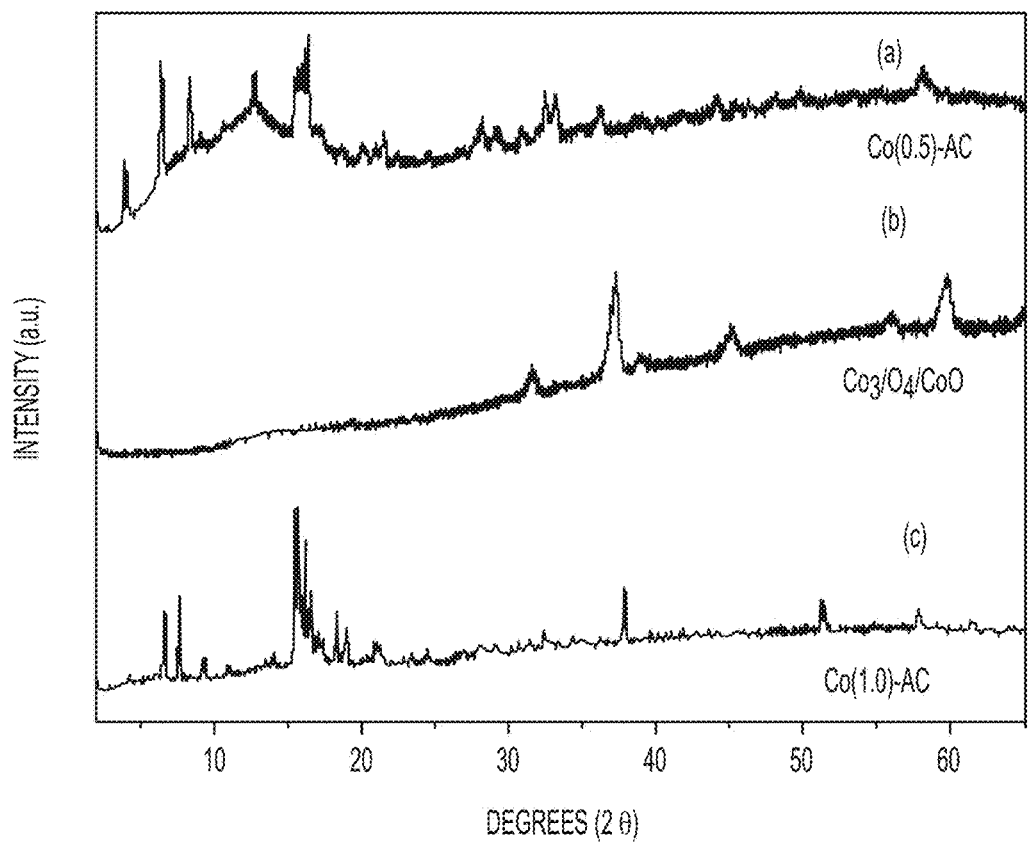
FIG. 1 includes stacked PXRD patterns of (a) a cobalt adamantane carboxylate compound formed from $Co(OH)_2$ and 1-adamantane carboxylic acid (ACA) with a 0.5:1 molar ratio of $Co^{2+}$ to ACA; (b) a cobalt oxide nanocomposite formed by thermally decomposing the compound of (a); and (c) a cobalt adamantane carboxylate compound formed from $Co(OH)_2$ and ACA with a 1.0:1 molar ratio of $Co^{2+}$ to ACA.

The diamondoids and their derivatives have shown promise in various applications such as in supramolecular, petrochemical, and medicinal chemistry. Compounds prepared according to methods embodied in this specification unite the chemistries of transition-metal oxides (TMOs) and diamondoids to form materials such as salts and nanocomposites incorporating transition metals or their oxides.

As used in this specification, the term "transition metal" refers to elements in periods 4, 5, and 6 and groups 4-12 of the periodic table of the elements, as defined by IUPAC in the 1990 edition of Nomenclature of Inorganic Chemistry.

As used in this specification, the term "diamondoid" refers to any chemical compound containing at least one adamantane moiety.

Reference will now be made in detail to embodiments of methods for preparing transition-metal adamantane carboxylate salts and nanocomposites that are derived from the transition-metal adamantane carboxylate salts and contain transition-metal oxide particles.

Methods for preparing a transition-metal adamantane carboxylate salt include mixing a transition-metal hydroxide and a diamondoid compound having at least one carboxylic acid moiety to form a reactant mixture.

In the reactant mixture, the transition-metal hydroxide may be a compound of the formula $M(OH)_x$, where M is a transition metal and x is equal to the oxidation state of the transition metal. In some embodiments, the transition-metal hydroxide may be chosen from compounds of the formula $M(OH)_2$, where M is a transition metal in a +2 oxidation state. In some embodiments, the transition-metal hydroxide may be chosen from compounds of the formula $M(OH)_2$, where M is chosen from Co, Cu, and Ni.

In the reactant mixture, the diamondoid compound has at least one carboxylic acid moiety. In some embodiments, the at least one carboxylic acid is bonded to any non-bridgehead carbon atom of the diamondoid compound. In some embodiments, the diamondoid compound may be chosen from carboxylic acids of adamantane, diamantane, or triamantane. In some embodiments, the diamondoid compound may be adamantane 1-carboxylic acid (ACA).

The mixing of the transition-metal hydroxide and the diamondoid compound may be performed by any suitable method using any suitable apparatus to accomplish intimate mixing. For example, the mixing may be performed using solid-state techniques such as blending or grinding of dry powders. The mixing may be performed with the aid of an aqueous or organic solvent by combining powders and the solvent and subsequently stirring the resultant solution. Optionally, after such a wet mixing procedure, some or all of the solvent may be decanted or filtered from the resultant mixture before the transition-metal hydroxide and the diamondoid compound are placed under conditions suitable for their chemical reaction.

The methods for preparing a transition-metal adamantane salt further include hydrothermally treating the reactant mixture of the transition-metal hydroxide and the diamondoid compound at a reaction temperature for a reaction time to form the transition-metal adamantane salt. Hydrothermal treatment generally may include adding an aqueous solvent such as water to the reaction mixture, sealing the reaction mixture in a reaction vessel such as an autoclave, and heating the reaction vessel to the reaction temperature to cause crystallization of the transition-metal adamantane salt to occur in a high-pressure environment.

The reaction temperature is chosen to provide sufficient thermodynamic energy for the reaction of the transition-metal hydroxide and the diamondoid compound to proceed within the reaction vessel while also enabling crystallization of the transition-metal adamantane salt. The reaction temperature should be sufficiently high to enable the reaction to progress but also be sufficiently low to avoid decomposition of the adamantane salt or solvation of crystallites. In some embodiments, the reaction temperature may be from 100° C. to 200° C., such as 100° C., 110° C., 120° C., 130° C., 140° C., 150° C., 160° C., 170° C., 180° C., 190° C., 200° C., or any other temperature between 100° C. and 200° C. Though in some embodiments the reaction temperature may be from 100° C. to 200° C., it is contemplated that other reactions may occur at temperatures lower than 100° C. or higher than 200° C. In other embodiments, the reaction temperature may be from 100° C. to 150° C. or from 110° C. to 150° C. In one example, where the transition metal hydroxide is $Co(OH)_2$ or $Cu(OH)_2$, the reaction temperature may be 110° C.±10° C. In another example, where the transition metal hydroxide is $Ni(OH)_2$, the reaction temperature may be 150° C.±10° C.

The reaction time is chosen to provide sufficient time for crystal growth and development of well-defined morphologies to occur as the transition-metal adamantane salt is formed at the reaction temperature. In some embodiments, the reaction time may be longer than 12 h, such as from 12 h to 72 h, from 24 h to 72 h, from 12 h to 48 h, or from 24 h to 48 h, for example. Though in some embodiments the reaction time may be longer than 12 h, it is contemplated that when higher reaction temperatures above 150° C. are chosen, for example, the reaction time may be shorter than 12 h.

The methods for preparing a transition-metal adamantane carboxylate salt may further include customary isolation steps such as cooling or depressurizing the reaction vessel, removing the reaction mixture from the reaction vessel, removing solvent from the reaction mixture by filtering or any other suitable technique, washing the transition-metal adamantane carboxylate salt with an aqueous or organic solvent that does not dissolve the transition-metal adamantane salt, drying the transition-metal adamantane carboxylate salt, or any combination of these steps. In some embodiments, the transition-metal adamantane carboxylate salt may be vacuum filtered from any solvent present in the reaction vessel, washed with water, and dried at a suitable temperature for a suitable time. For example, the transition-metal adamantane carboxylate salt may be dried at 65° C. for 24 h to drive off residual solvent from the hydrothermal treatment.

The transition-metal adamantane carboxylate salt prepared using a transition-metal hydroxide $M(OH)_2$ and ACA will be subsequently described by a shorthand notation M(x)-AD, where M is a transition metal, x is the ratio of M and ACA in the reaction mixture used to prepare the transition-metal adamantane carboxylate salt, and AC represents the carbon support derived from the adamantane moiety of the ACA. For example, Co(0.5)-AC represents a cobalt adamantane carboxylate salt prepared by reacting $Co(OH)_2$ and ACA with a 0.5:1 molar ratio of $Co^{2+}$ to ACA. Likewise, Co(1.0)-AC represents a cobalt adamantane carboxylate salt prepared by reacting $Co(OH)_2$ and ACA with a 1.0:1 molar ratio of $Co^{2+}$ to ACA. Likewise, Ni(0.5)-AC represents a nickel adamantane carboxylate salt prepared by reacting $Ni(OH)_2$ and ACA with a 0.5:1 molar ratio of $Ni^{2+}$ to ACA. Likewise, Cu(0.5)-AC represents a copper adamantane carboxylate salt prepared by reacting $Cu(OH)_2$ and ACA with a 0.5:1 molar ratio of $Cu^{2+}$ to ACA. Likewise, Cu(1.0)-AC represents a copper adamantane carboxylate salt prepared by reacting $Cu(OH)_2$ and ACA with a 1.0:1 molar ratio of $Cu^{2+}$ to ACA.

In some embodiments, the reaction mixture may be prepared by mixing a transition metal hydroxide compound of formula $M(OH)_2$, where M is Co, Ni, or Cu, and ACA in amounts that provide a ratio of $M^{2+}$ to ACA in the reaction mixture of from 0.5:1 to 1.0:1. The specific ratio of $M^{2+}$ to ACA in the reaction mixture may be chosen to affect the overall crystal morphology of the transition-metal adamantane salt to a desired form. Without intent to be bound by theory, it is believed that the crystal morphology of the transition-metal adamantane salt may be tailored by increasing or decreasing the ratio of $M^{2+}$ to ACA in the reaction mixture. Though in some embodiments the ratio of $M^{2+}$ to ACA may be selected from 0.5:1 to 1.0:1, it is contemplated that the crystal morphology of the transition-metal adamantane salt may be further tailored by decreasing the ratio of $M^{2+}$ to ACA to below 0.5:1 or by increasing the ratio of $M^{2+}$ to ACA to greater than 1.0:1. Even so, a point of saturation is believed to exist, above which additional transition-metal ions cannot be incorporated into the transition-metal adamantine carboxylate salt.

Further embodiments of this specification are directed to methods for preparing nanocomposites. The methods for preparing the nanocomposites include thermally decomposing a transition-metal adamantane carboxylate salt prepared according to the methods previously described in this specification. In some embodiments, the nanocomposites include transition-metal oxide particles or structures supported on a carbon framework derived from the diamondoid compound.

In some embodiments, thermally decomposing the transition-metal adamantane carboxylate salt may include heating the transition-metal adamantane carboxylate salt. The heating of the transition-metal adamantine carboxylate salt may be conducted, for example, in air at a decomposition temperature for a decomposition time. The decomposition temperature and the decomposition time may be selected to result in complete decomposition of the transition-metal adamantane carboxylate salt. Complete decomposition of the transition-metal adamantine carboxylate salt may include conversion of any transition-metal hydroxide functionalities in the adamantane carboxylate salt to transition-metal oxide particles. Suitable decomposition temperatures may be greater than 200° C., greater than 300° C., greater than 400° C., or greater than 500° C., for example. The decomposition time may be chosen as any time sufficient to result in complete decomposition of the transition-metal adamantane carboxylate salt at the chosen decomposition temperature. For example, the decomposition time may be longer than 1 hour, such as 2 hours, 3 hours, 4 hours, or longer than 5 hours. In example embodiments, transition-metal adamantine carboxylate salts formed from $M(OH)_2$ and ACA, where M is Co, Ni, or Cu, may decompose fully at a decomposition temperature of about 450° C. and a decomposition time of at least 4 hours.

Nanocomposites formed by thermally decomposing the transition-metal adamantane carboxylate salts may exhibit a variety of crystal morphologies that may depend on variables such as the ratio of transition-metal hydroxide to diamondoid compound in the reaction mixture used to form the transition-metal adamantane carboxylate salt, the reaction time and temperature used to form the transition-metal adamantine carboxylate, and the decomposition conditions used to form the nanocomposite itself.

In some embodiments, the methods for preparing nanocomposites include thermally decomposing transition-metal adamantane carboxylate salts prepared by reacting transition-metal hydroxides $M(OH)_2$ and ACA, where M is chosen from Co, Ni, and Cu. Nanocomposites formed from such transition-metal adamantane carboxylate salts may include transition-metal oxide particles $MO_x$ of a particular shape or morphology dispersed on a carbon support of a particular shape or morphology. For example, in embodiments where M is Co, the metal oxide particles may include CoO, $Co_3O_4$, or a mixture of CoO and $Co_3O_4$. In embodiments where M is Ni, the metal-oxide particles may include NiO. In embodiments where M is Cu, the metal-oxide particles may include CuO, $Cu_2O$, or a mixture of CuO and $Cu_2O$. The metal-oxide particle may be spherical, rectangular, ribbon-like, or in the form of nanowires, nanorods, or nanowhiskers, for example. The transition-metal oxide particles may have particle sizes from 10 nm to 20 nm, for example. Likewise, the carbon support may exhibit a morphology such as a sheet, a nanorod, a nanowire, a nanorod, or a nanowhisker.

In some embodiments, the transition-metal oxide particles may be uniformly dispersed over a surface of a carbon support derived from the adamantane moieties of the transition-metal adamantane carboxylate salt. The weight fraction of metal-oxide particles and carbon support may vary in the nanocomposite, depending on the conditions used to prepare the nanocomposite. In some embodiments, the nanocomposite may include from 50 wt. % to 90 wt. % metal oxide particles and from 10 wt. % to 50 wt. % carbon, based on the total weight of the nanocomposite. For example, the nanocomposite may include from 70 wt. % to 80 wt. % metal oxide particles and from 20 wt. % to 30 wt. % carbon, based on the total weight of the nanocomposite.

In some embodiments, the nanocomposite may be formed by thermally decomposing a cobalt-adamantane carboxylate salt (Co-AC) prepared as previously described. Examples of such nanocomposites may have a microporous matrix and crystallites of cobalt oxide interspersed within the microporous matrix. The microporous matrix may include carbon derived from the adamantane moieties of the cobalt-adamantane carboxylate salt.

In some embodiments, the nanocomposite may be formed by thermally decomposing a nickel-adamantane carboxylate salt (Ni-AC) prepared as previously described. Examples of such nanocomposites include porous nanowhiskers of nickel oxide particles connected to a carbon support derived from the adamantane moieties of the nickel-adamantane carboxylate salt.

In some embodiments, the nanocomposite may be formed by thermally decomposing a copper-adamantane carboxylate salt (Cu-AC) prepared as previously described. Examples of such nanocomposites may have a microporous matrix and crystallites of copper oxide supported on carbon sheets. The carbon sheets may include carbon derived from the adamantane moieties of the copper-adamantane carboxylate salt.

Further embodiments of this specification are directed to catalyst systems. The catalyst systems may include (a) a transition-metal adamantine carboxylate salt prepared according to any embodiment previously described; (b) a transition-metal oxide particle supported on carbon prepared according to any embodiment previously described, such as by thermal decomposition of a transition-metal adamantine carboxylate salt; or (c) any catalytically active mixture of (a) and (b).

Accordingly, further embodiments of this specification are directed to methods for catalyzing a chemical reaction between at least one first reactant and at least one second reactant. Such methods may include reacting the at least one first reactant and at least one second reactant in the presence of a catalyst system described above. The at least one first reactant and the at least one second reactant may be any chemical compounds, the chemical reaction of which is catalytically facilitated, such as by being made thermodynamically possible or more favorable, or kinetically influenced by the presence of the transition-metal adamantane carboxylate salt or the nanocomposite separately or in combination. In example embodiments, the chemical reaction may be an alcohol oxidation or a cross-coupling reaction that forms at least one carbon-nitrogen bond.

Still further embodiments of this specification are directed to methods for catalyzing the decomposition of a reactant. Such methods may include decomposing the reactant in the presence of a catalyst system described above. The decomposing of the reactant may be conducted under milder conditions than those generally known to decompose the reactant, such as under a decreased decomposition temperature, a decreased decomposition time, or a decreased decomposition pressure.

Still further embodiments of this specification are directed to polymer composites that contain at least one polymer or copolymer in combination with at least one filler compound interspersed among the at least one polymer or copolymer to form a composite. In such embodiments, the at least one filler compound may be chosen from (a) a transition-metal adamantane carboxylate salt prepared according to any embodiment previously described; (b) a transition-metal oxide particle supported on carbon prepared according to any embodiment previously described, such as by thermal decomposition of a transition-metal adamantane carboxylate salt; or (c) any mixture of (a) and (b).

Still further embodiments of this specification are directed to systems for removing a chemical compound from a fluid stream such as a liquid stream, a gas stream, or a slurry containing a liquid and a solid. The systems may include an adsorbent chosen from: (a) a transition-metal adamantane carboxylate salt prepared according to any embodiment previously described; (b) a transition-metal oxide particle supported on carbon prepared according to any embodiment previously described, such as by thermal decomposition of a transition-metal adamantane carboxylate salt; or (c) any mixture of (a) and (b). The systems may further include any suitable vessel in which, or any active surface on which, the chemical compound in the fluid stream is contacted with the adsorbent so as to be adsorbed onto the adsorbent and removed from the fluid stream.

Still further embodiments of this specification are directed to drilling fluids, such as a drilling fluid appropriate for use in the petroleum industry. Such drilling fluids may include at least one rheology modifier chosen from (a) a transition-metal adamantane carboxylate salt prepared according to any embodiment previously described; (b) a transition-metal oxide particle supported on carbon prepared according to any embodiment previously described, such as by thermal decomposition of a transition-metal adamantane carboxylate salt; or (c) any mixture of (a) and (b).

Thus, embodiments of transition-metal diamondoid salts, nanocomposites of carbon-supported transition-metal oxide particles have been described, along with further embodiments of catalytic systems and methods, polymer composites, systems for removing chemical compounds from fluid streams, and drilling fluids incorporating one or more of the transition-metal diamondoid salts or nanocomposites. In example embodiments, 1-adamantane carboxylate was used as a structure directing agent to generate the transition metal compounds having varied morphologies. The thermal decomposition or calcination of such compounds results in an in situ generation of carbon-supported transition-metal oxides.

EXAMPLES

The embodiments described in the Detailed Description will be further clarified by the following Examples. It should be understood that the following Examples are not intended to limit the scope of this disclosure or its claims to any particular embodiment.

As described in Examples 1, 3, and 5, transition-metal adamantane compounds according to embodiments of this disclosure were prepared by hydrothermally treating a transition-metal hydroxide with 1-adamantane carboxylic acid. In the following example preparations, a metal hydroxide and adamantane carboxylic acid were stirred for one hour before being transferred into a reaction vessel. The resultant mixture was hydrothermally treated at different temperatures for 24 h. The resultant products were vacuum filtered and washed with copious amount of water, then dried at 65° C. for 24 h.

As described in Examples 2, 4, and 6, transition-metal oxides were prepared from the transition-metal adamantane compounds by thermally decomposing the adamantane compounds at 450° C. for 4 h under air atmosphere. Products were characterized by powder X-ray diffraction (PXRD), infra-red (IR) spectroscopy, scanning electron microscopy (SEM), thermogravimetric analysis (TGA), and transmission electron microscopy (TEM).

Example 1

Synthesis and Characterization of Cobalt Adamantanes

Co-adamantane carboxylate salts (Co-AC) were synthesized by treating $Co(OH)_2$ and 1-adamantane carboxylic acid (ACA) under hydrothermal conditions at 110° C. for 24 h. Prior to the reaction, the reactants were intimately mixed by stirring for 1 h using a magnetic stirrer. Two Co-AC compounds were synthesized with different molar ratios of $Co^{2+}$ to ACA to evaluate the effects of supersaturation on phase formation and the morphology of the resultant phase. A first compound, Co(0.5)-AC, was synthesized using a 0.5 molar ratio of $Co^{2+}$ to ACA. A second compound, Co(1.0)-AC, was synthesized using a 1.0 molar ratio of $Co^{2+}$ to ACA. The compounds were characterized using various analytical techniques.

The PXRD pattern of Co(0.5)-AC is provided as spectrum (a) of FIG. 1. Low angle reflections were observed at 2θ angles of 4.27°, 6.08°, 6.65°, 7.50°, 9.31°, and 10.91°. These low-angle reflections indicate d-spacings of 20.67 Å, 14.52 Å, 13.28 Å, 11.77 Å, 11.50 Å, and 8.1 Å, respectively. The Co(0.5)-AC showed several reflections with varied intensities up to a 2θ angle of 65°.

Figure 2:
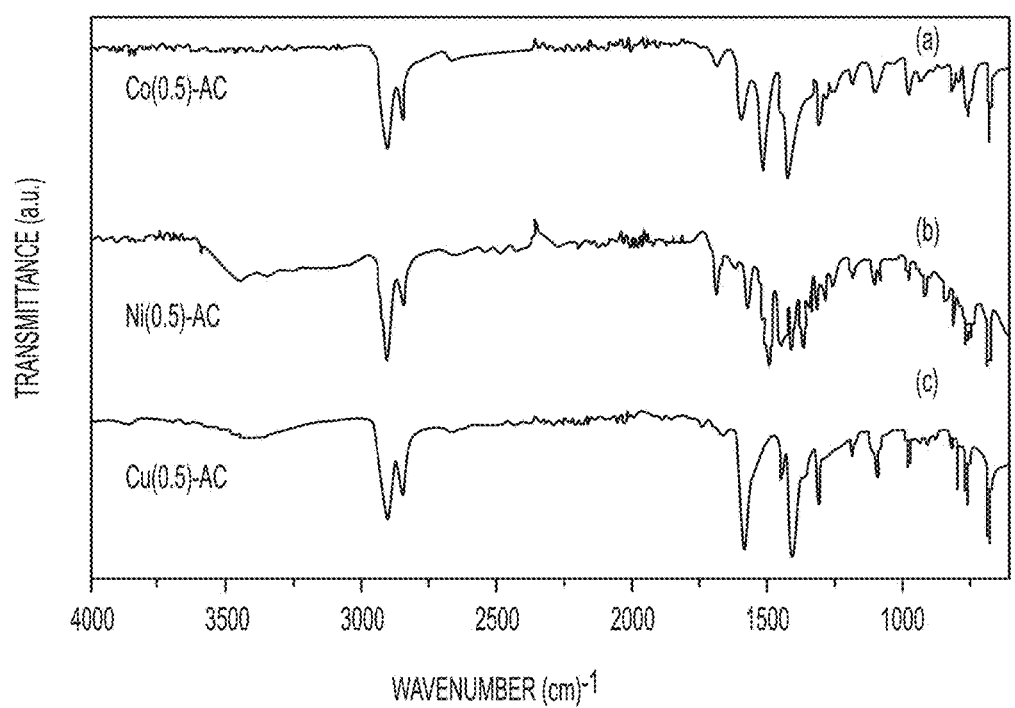
FIG. 2 includes stacked IR spectra of adamantane carboxylate compounds formed from (a) $Co(OH)_2$ and ACA with a 0.5:1 molar ratio of $Co^{2+}$ to ACA; (b) a nickel adamantane carboxylate compound formed from $Ni(OH)_2$ and ACA with a 0.5:1 molar ratio of $Ni^{2+}$ to ACA; and (c) a copper adamantane carboxylate compound formed from $Cu(OH)_2$ and ACA with a 0.5:1 molar ratio of $Cu^{2+}$ to ACA.

The IR spectrum of Co(0.5)-AC is provided as spectrum (a) of FIG. 2, which shows various distinct stretching and bending vibrations. The vibrations at 2904 $cm^{-1}$ and 2846 $cm^{-1}$ arise from stretching modes of C—H of the adamantane ion. Symmetric and antisymmetric vibrations of the $COO^-$ group of adamantane are seen at 1508 $cm^{-1}$ and 1422 $cm^{-1}$. The multiple stretching and bending modes below 1000 $cm^{-1}$ arise from metal-oxygen bonds. The hydroxyl ion region 3200 $cm^{-1}$ to 3700 $cm^{-1}$ is nearly featureless, indicating an absence of hydroxyl ions in the compound. The vibration at around 1603 $cm^{-1}$ may arise from the bending mode of water molecules in Co-AC.

The thermal stability of the Co(0.5)-AC was studied under $N_2$ atmosphere from 25° C. to 800° C. using TGA. The Co(0.5)-AC shows a two-step mass loss as shown in plot (a) of FIG. 3. The material was found to be stable up to 100° C. without losing any mass. The material lost about 22 wt. % of its mass in the range 100° C. to 180° C., which could include loosely bound water molecules along with some other residues, believed to be components of the adamantane moiety. The material was stable from 180° C. to 400° C. with negligible amount of mass loss and then it lost around 65 wt. % of its mass in the second step (400° C. to 550° C.). A small and steady mass loss was apparent from 550° C. to 800° C., and the material completely decomposed at 800° C. The Co-AC lost around 85 wt. % of mass from 25° C. to 800° C., indicating the formation of nanoporous oxides of cobalt. The TGA of the Co(0.5)-AC shows that Co(0.5)-AC is not a high-temperature stable phase but could be a precursor for nanoporous oxides of cobalt. The significant mass loss of around 85 wt. % indicates that the Co-AC is made up of a large amount of decomposable adamantane moiety.

Figure 4A:
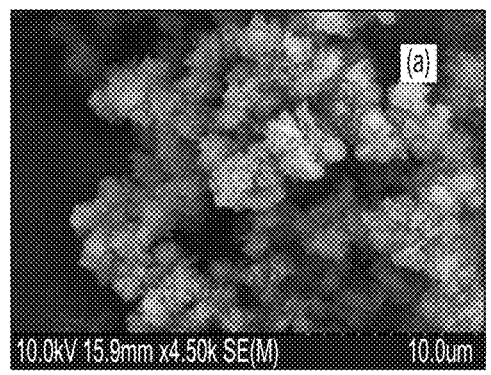
FIGS. 4A-4D are SEM micrographs of a cobalt adamantane carboxylate compound formed from $Co(OH)_2$ and ACA with a 0.5:1 molar ratio of $Co^{2+}$ to ACA.
Figure 4B:
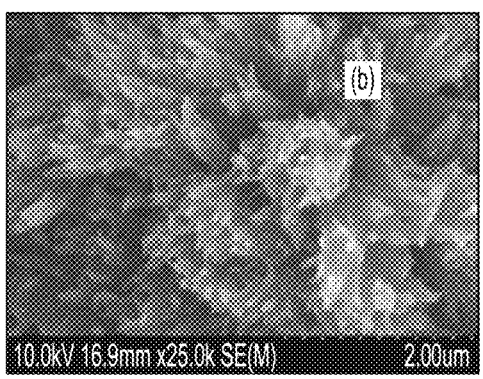

The morphology of the Co(0.5)-AC was characterized by SEM, as shown in FIGS. 4A and 4B. Co-AC shows an interesting fibrous nature, with each fiber being interconnected with an adjacent one, resulting in the formation of spheres of fibers. It is believed that the adamantane backbone may be the reason for the tendency to form spheres.

$Co^{2+}$ has the tendency to form α-hydroxides and hydroxy salts with various inorganic/organic anions. Both these compounds are made up of hydroxide layers, exhibiting interlayer chemistry. The anions intercalated in the interlayer mediate the various properties of these compounds. Similarly, Co(0.5)-AC would have adopted one of these two structures by using adamantane carboxylate ion as anion. The data from IR spectrum clearly shows the absence of the $OH^-$ ion, ruling out the crystallization of Co-AC in an α-hydroxide/hydroxy salt structure. Considering all the data from PXRD, IR, TGA, and SEM it its believed that the Co-AC may have a structure of $Co^{2+}$ binding with two carboxylate ions of two adamantane carboxylic acid molecules, which together form a salt of cobalt having a layered structure.

The effect of supersaturation on the formation of Co-AC was evaluated by preparing a sample of Co(1.0)-AC using the same synthetic route as previously described for Co(0.5)-AC with reduction of the amount of 1-adamantane carboxylate to begin with a 1:1 molar ratio of $Co^{2+}$ to ACA.

The PXRD pattern of Co(1.0)-AC is provided as plot (c) of FIG. 1. Similarly to the Co(0.5)-AC sample, the Co(1.0)-AC was found to exhibit low-angle reflections at 2θ angles of 3.96°, 6.4°, 8.35°, and 12.77°. These low-angle reflections indicate d-spacings of 22.3 Å, 13.8 Å, 10.58 Å, and 6.9 Å, respectively. The intensity of the reflections were much stronger for Co(1.0)-AC than in Co(0.5)-AC (see plot (a) of FIG. 1), indicating better crystal growth in case of Co(1.0)-AD. The PXRD of Co(1.0)-AC was expected to show some unreacted $Co(OH)_2$, because cobalt was in excess in the reaction mixture. An absence of reflections attributable to $Co(OH)_2$ suggests that the $Co(OH)_2$ may have dissolved in the reaction medium or was obscured under the background in the PXRD.

Figure 4C:
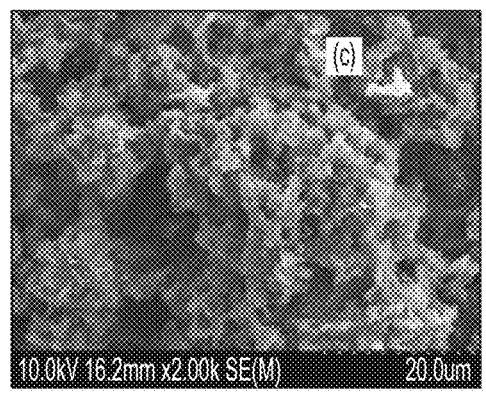
Figure 4D:
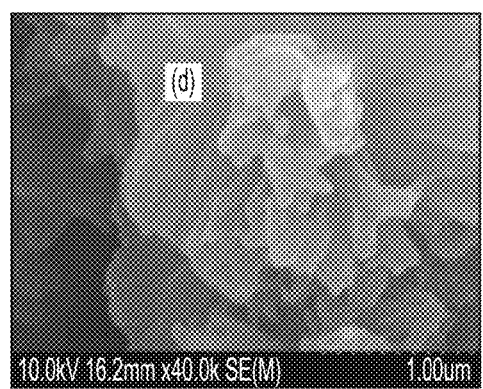

The morphology of the Co(1.0)-AC was characterized by SEM and is illustrated in FIGS. 4C and 4D. The Co(1.0)-AC exhibited a similar morphology to that of Co(0.5)-AC. The SEM also shows hexagonally faceted crystals, believed to be unreacted $Co(OH)_2$.

Example 2

Cobalt Oxide from Thermal Decomposition of Cobalt Adamantane Carboxylate Salts The Co(0.5)-AC, on calcination is expected to give $Co_3O_4$/CoO supported on the carbon residue of adamantane. Co(0.5)-AC prepared according to Example 1 was decomposed at 450° C. for 4 h under air atmosphere.

The PXRD of the resultant oxide material is provided as plot (b) of FIG. 1. The PXRD showed reflections at 2θ angles of 19.23°, 31.63°, 37.13°, 38.9°, 45.1°, 55.91°, and 59.63°. These reflections indicate d-spacings of 4.61 Å, 2.82 Å, 2.41 Å, 2.31 Å, 2.0 Å, 1.64 Å and 1.54 Å, respectively. The reflections of the prepared sample were determined to be more consistent with literature reports of $Co_3O_4$ rather than of CoO. A broad hump centered around 14° in the PXRD of the oxide sample could not be assigned to any phase of cobalt oxide. The origin of this broad hump is believed to arise from residual carbon present in the sample that creates a layered material.

Figure 5A:
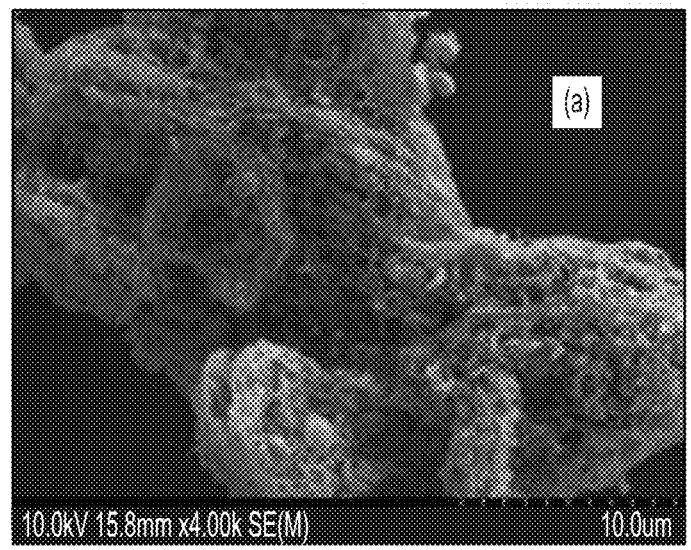
FIGS. 5A and 5B are SEM micrographs of a cobalt oxide nanocomposite formed from thermal decomposition of a cobalt adamantane carboxylate compound formed from $Co(OH)_2$ and ACA with a 0.5:1 molar ratio of $Co^{2+}$ to ACA.
Figure 5B:
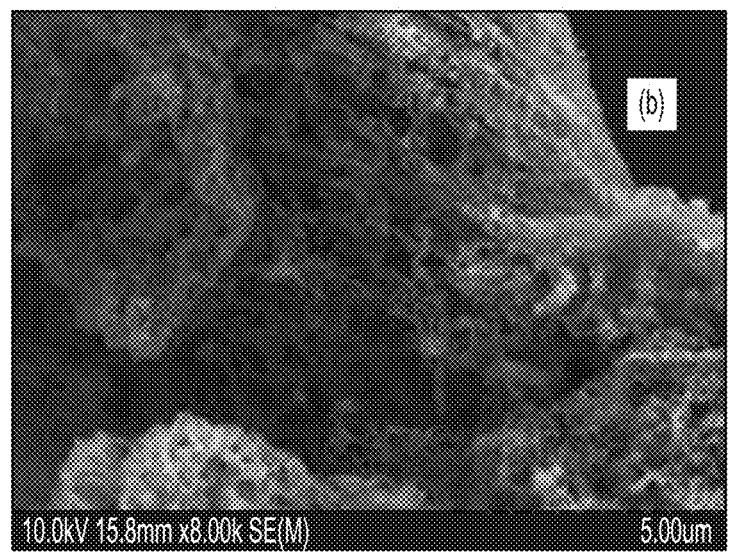

The oxide residue of Co(0.5)-AC was further characterized using SEM. As illustrated in FIGS. 5A and 5B, the resultant oxide was found by SEM to have a microporous, sponge-like morphology. The oxide crystallites were found to grow as nanowires, which in turn form a highly porous network having very large pores.

The EDX technique was used to establish the presence of the carbon in the oxide obtained from Co-adamantane carboxylate salt decomposition. To avoid interference of the substrate carbon with the carbon in the sample, a silicon wafer was used as a substrate during the SEM. As expected, the EDX analysis showed peaks attributable to $Co^{2+}$, $Co^{3+}$ and oxygen from the cobalt oxide. In addition, the EDX showed a peak attributable to the elemental carbon, thus indicating the presence of a significant amount of carbon in the sample. To assess the distribution of the carbon in the cobalt oxide, elemental mapping was carried out using an SEM/EDX technique. Within the elemental mapping, the carbon was found to be spread uniformly across the whole of oxide residue.

Figure 6A:
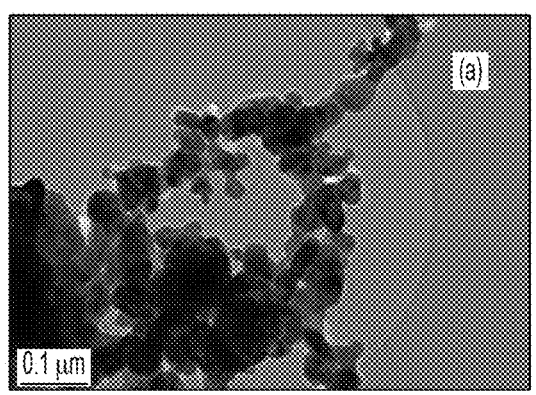
FIGS. 6A and 6B are TEM micrographs of a cobalt oxide nanocomposite formed from thermal decomposition of a cobalt adamantane carboxylate compound formed from $Co(OH)_2$ and ACA with a 0.5:1 molar ratio of $Co^{2+}$ to ACA.
Figure 6B:
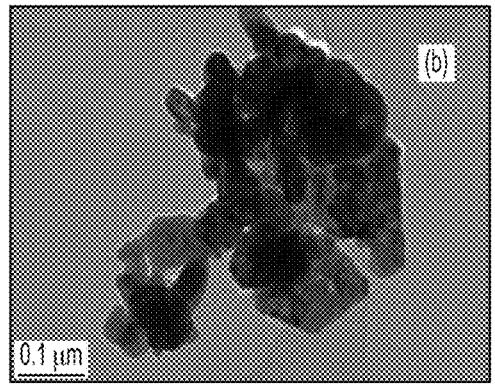
Figure 6C:
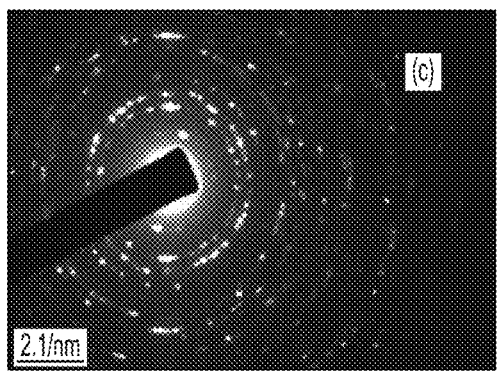
FIG. 6C is a selected-area diffraction pattern of the cobalt nanocomposite of FIGS. 6A and 6B.
Figure 6D:
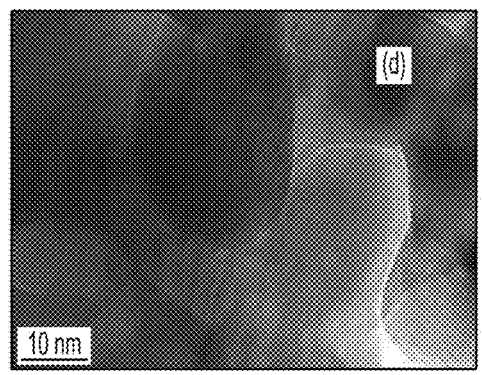
FIG. 6D is a HRTEM micrograph of the cobalt nanocomposite of FIGS. 6A and 6B.

The size and shape of the cobalt oxide crystallites were characterized by TEM (FIGS. 6A-6D). The cobalt oxides were observed to have crystallite sizes in the range of 10 nm to 20 nm, as shown by bright-field TEM images (FIGS. 6A and 6B). The selected area diffraction pattern shows multiple diffraction rings matching with the d-spacing of $Co_3O_4$ (FIG. 6C). The lattice fringes of the cobalt oxide were observed by HRTEM (FIG. 6D).

Example 3

Synthesis and Characterization of Nickel Adamantane Carboxylate Salts

Ni-adamantane carboxylate (Ni-AC) was synthesized by treating $Ni(OH)_2$ and 1-adamantane carboxylic acid in a 0.5:1 molar ratio of $Ni^{2+}$ to ACA, under hydrothermal conditions at 150° C. for 24 h. Prior to the reaction, the reactants were intimately mixed by stirring for 1 h using a magnetic stirrer. The resultant material, Ni(0.5)-AC, was characterized by PXRD, IR, TGA, and SEM.

Figure 7:
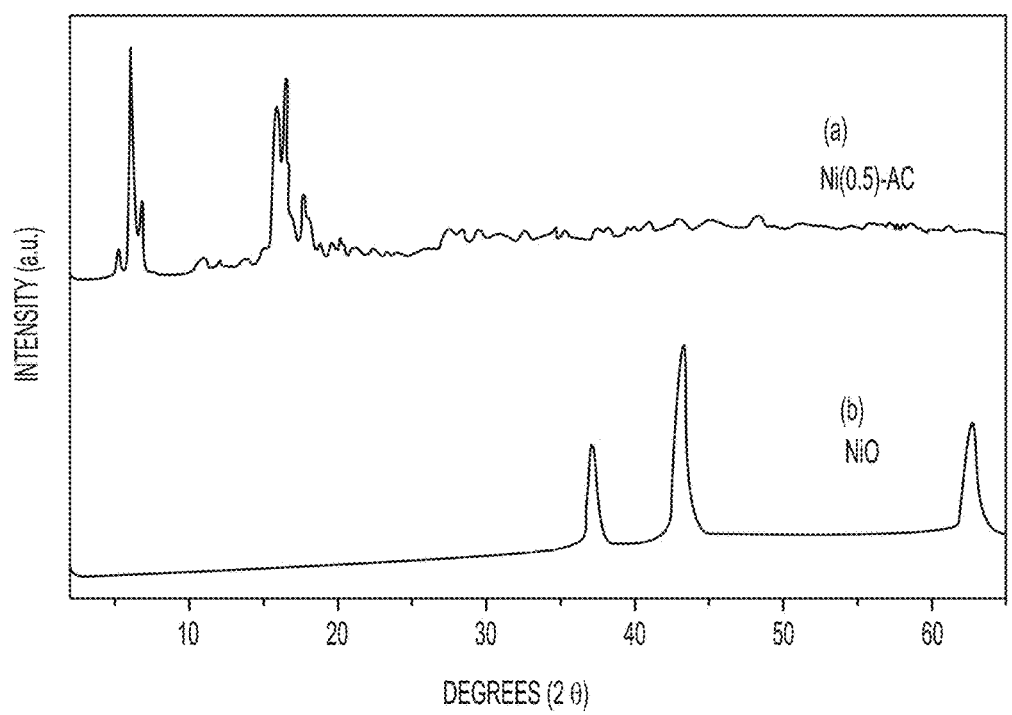
FIG. 7 shows stacked PXRD spectra of (a) a nickel adamantane carboxylate compound formed from $Ni(OH)_2$ and ACA with a 0.5:1 molar ratio of $Ni^{2+}$ to ACA; and (b) a nickel oxide nanocomposite formed by thermally decomposing the compound of (a).
Figure 8A:
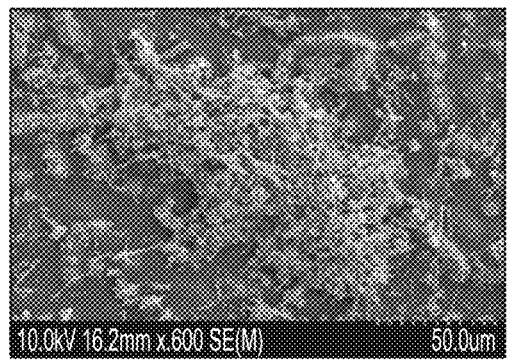
FIGS. 8A-8D are SEM micrographs of a nickel adamantane carboxylate compound formed from $Ni(OH)_2$ and ACA with a 0.5:1 molar ratio of $Ni^{2+}$ to ACA.
Figure 8B:
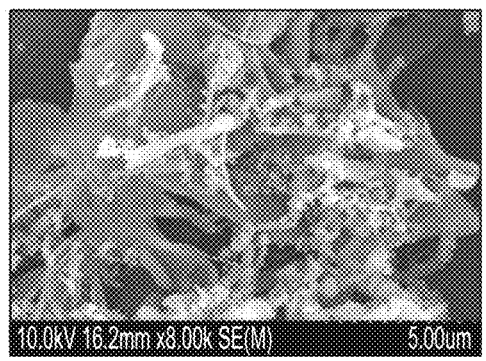
Figure 8C:
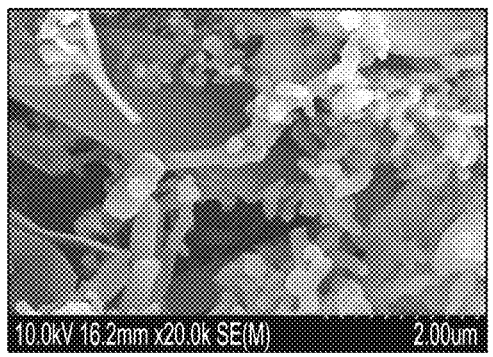
Figure 8D:
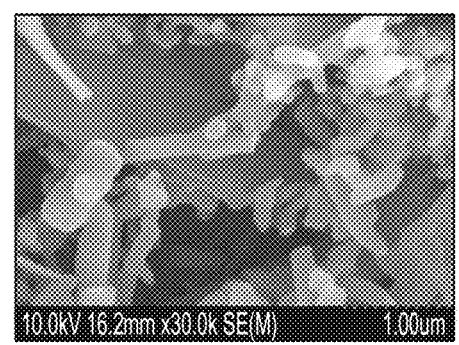

The PXRD spectrum of Ni(0.5)-AC in plot (a) of FIG. 7 exhibited a series of low-angle reflections at 2θ angles of 5.33°, 6.11°, 6.32°, and 7.87°. These low-angle reflections indicated d-spacings of 16.56 Å, 14.45 Å, 13.97 Å, and 13.06 Å, respectively. The low-angle reflections showed second submultiples at 8.30 Å, 7.97 Å, 7.34 Å, and 6.48 Å. The PXRD also exhibited higher submultiples of the low-angle reflections at higher 2θ values. The appearance of the submultiples is consistent with Ni-AC having crystallized in a layered structure.

The IR spectrum of the Ni(0.5)-AC is provided in plot (b) of FIG. 2 and shows various stretching and bending vibrations. The vibrations at 2904 $cm^{-1}$ and 2847 $cm^{-1}$ arise from stretching modes of C—H of the adamantane carboxylate ion. Symmetric and antisymmetric vibrations of $COO^-$ groups of adamantane carboxylate are seen at 1566 $cm^{-1}$ and 1489 $cm^{-1}$. The multiple stretching and bending modes less than 1000 $cm^{-1}$ arise from metal-oxygen bonds. A broad hump with a sharp peak at 3449 $cm^{-1}$ indicates the presence of hydrogen-bonded hydroxy ion in the compound. The vibration at about 1600 $cm^{-1}$ is believed to arise from a bending mode of water molecules and to indicate that the Ni(0.5)-AC has some water present.

Thermal stability of Ni(0.5)-AC was studied using TGA. The TGA data are provided as plot (b) of FIG. 3. The mass loss (~8 wt. %) around 60° C. is mainly attributed to the physisorbed water. The material shows gradual but steady mass loss of around 7 wt. % from 60° C. to 320° C., possibly as a result of small amounts of amorphous impurities present in the sample. The TGA shows a massive mass loss of around 70 wt. % in the range of 320° C. to 420° C. accounting for hydroxyls, carboxylates, H, and C of the Ni(0.5)-AC. In total, Ni(0.5)-AC loses around 90 wt. % from 25° C. to 800° C., leaving only 10 wt. % residue.

The Ni(0.5)-AC shows a layered morphology with tendency of layers to grow rods, as evident from the SEM images in FIGS. 8A-8D of the same material at different levels of magnification.

Example 4

Nickel Oxide from Thermal Decomposition of Nickel Adamantane Carboxylate Salts

Similar to how Co-AD yields oxides of cobalt on thermal decomposition, Ni-AC was expected to give oxides of nickel on a carbon support upon thermal decomposition. The Ni(0.5)-AC prepared according to Example 3 was decomposed from 25° C. to 450° C. for 4 h under air atmosphere. As illustrated in plot (b) of FIG. 7, the PXRD spectrum of the resultant oxide residue exhibited reflections at 2θ angles of 37.21°, 43.23°, and 62.9°, corresponding to 2.41 Å, 2.09 Å, and 1.47 Å, respectively. Based on comparisons with literature values, the nickel oxide residue was assigned to a NiO phase. The broad hump observed in the PXRD of $Co_3O_4$ (plot (b) of FIG. 1) is missing in NiO. Without intent to be bound by theory, it is believed that the absence of the broad hump may imply that (a) NiO doesn't have any carbon at all in it; or (b) the hump may have been obscured under the background of high-intensity reflections of NiO.

Figure 9A:
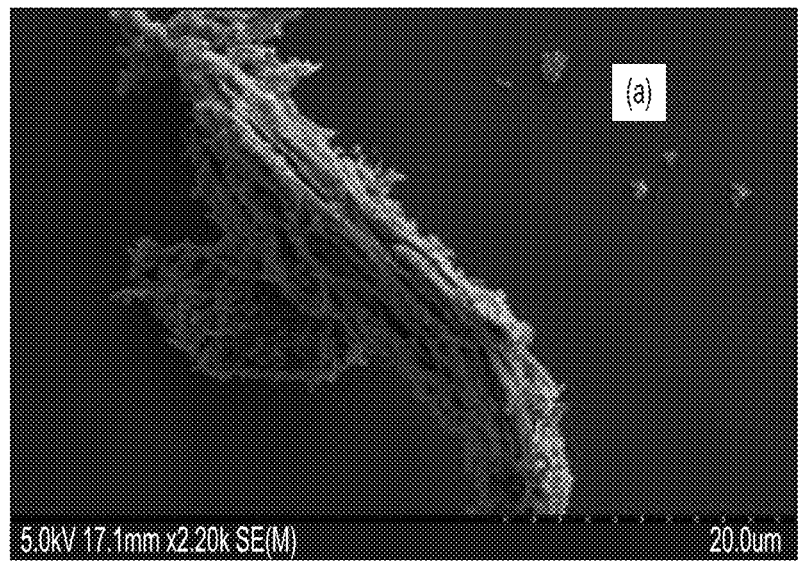
FIGS. 9A and 9B are SEM micrographs of a nickel oxide nanocomposite formed by thermally decomposing a nickel adamantane carboxylate compound formed from $Ni(OH)_2$ and ACA with a 0.5:1 molar ratio of $Ni^{2+}$ to ACA.
Figure 9B:
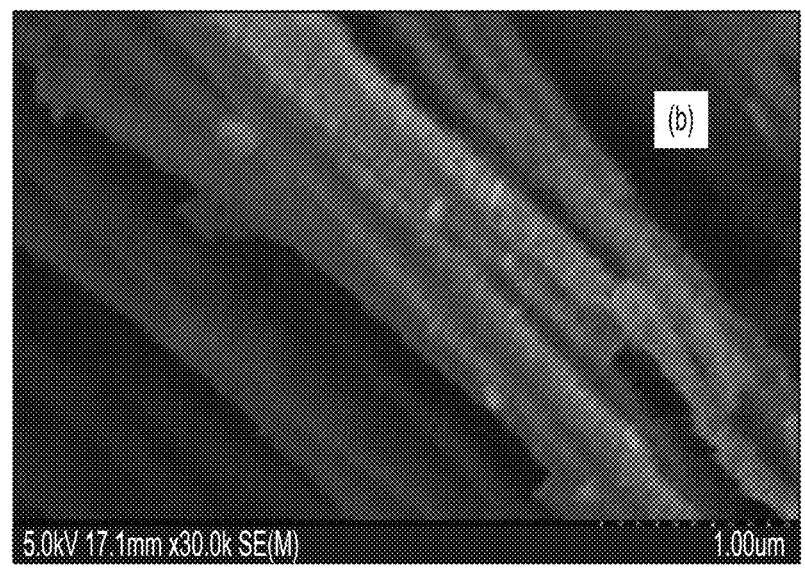

The template effect of incorporated adamantane observed in the formation of spongy, porous $Co_3O_4$ was expected for NiO as well. The SEM micrographs of NiO resulting from Ni(0.5)-AD (FIGS. 9A and 9B) portray a nanowhisker morphology. Individual crystallites of spherical NiO are arranged as nanowhiskers with micron length. Such an arrangement is believed to result in the highly porous nature of the nickel oxide. Without intent to be bound by theory, it is believed that the tendency of Ni-AC to form rod-like shapes, possibly owing to the arrangements of adamantanes, may give rise to the observed formation of highly porous nanowhiskers of NiO on thermal decomposition of the Ni-AC.

A qualitative elemental analysis of the NiO was undertaken using EDX. Integrated EDX spectra indicated the presence of Ni and O of the NiO in a molar ratio of about 1:1. The EDX spectra included also a peak attributed to elemental carbon. It is believed that the source of the carbon is the adamantane moiety from the Ni-AC material.

Figure 10A:
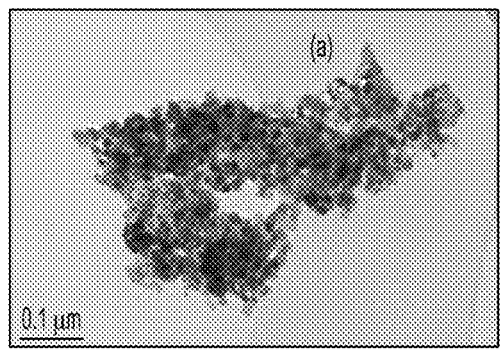
FIGS. 10A and 10B are bright-field TEM micrographs of a nickel oxide nanocomposite formed by thermally decomposing a nickel adamantane carboxylate compound formed from $Ni(OH)_2$ and ACA with a 0.5:1 molar ratio of $Ni^{2+}$ to ACA.
Figure 10B:
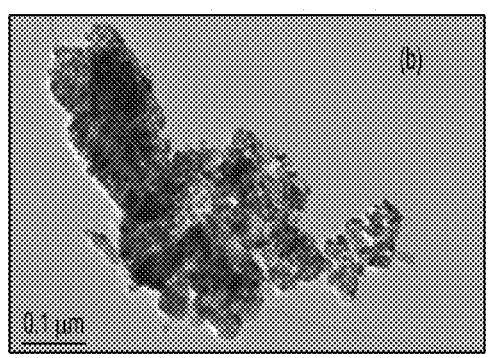
Figure 10C:
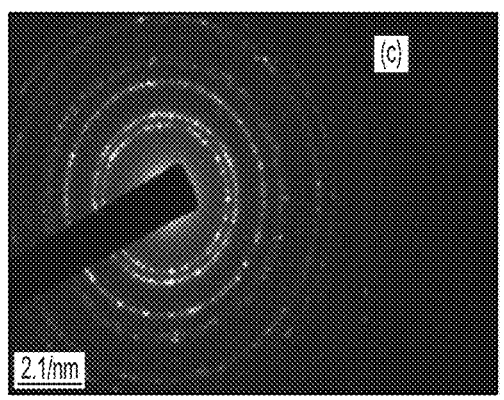
FIG. 10C is a selected-area electron diffraction pattern of the nickel oxide nanocomposite of FIGS. 10A and 10B.
Figure 10D:
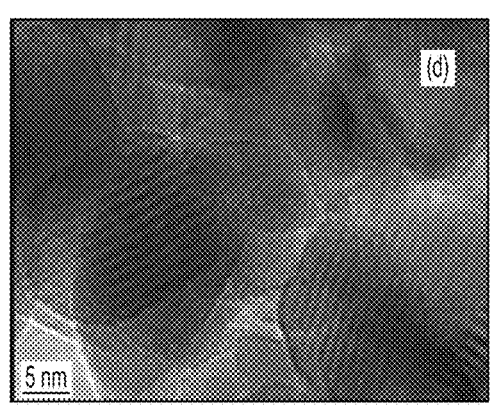
FIG. 10D is a HRTEM image of the nickel oxide nanocomposite of FIGS. 10A and 10B.

Nickel oxide obtained from Ni-AC was further characterized by TEM (FIGS. 10A-10D). The bright-field images of FIGS. 10A and 10B illustrate the tendency of NiO grow as whiskers having micron lengths. The selected area electron diffraction pattern of the nickel oxide derived from Ni(0.5)-AD in FIG. 10C is consistent with those reported in the literature for NiO. A high-resolution TEM (HRTEM) image of the nickel oxide in FIG. 10D illustrates lattice fringes of rock-salt structured NiO planes. In addition, the HRTEM shows the larger lattice fringes having d-spacings of approximately 1 nm that are not attributable to any NiO plane. These lattice fringes with higher d-spacing may be assigned to carbons of the adamantane carboxylate that remain present in the oxide residue.

Example 5

Synthesis and Characterization of Copper Adamantane Carboxylate Salts

Cu-adamantane carboxylate was synthesized by treating $Cu(OH)_2$ and 1-adamantane carboxylic acid under hydrothermal conditions at 110° C. Prior to the reaction, the reactants were stirred for 1 h on the magnetic stirrer to achieve intimate mixing. Two Cu-AC compounds were synthesized with different molar ratios of $Cu^{2+}$ to ACA to evaluate the effects of supersaturation on phase formation and the morphology of the resultant phase. A first compound, Cu(0.5)-AC, was synthesized using a 0.5 molar ratio of $Cu^{2+}$ to ACA. A second compound, Cu(1.0)-AC, was synthesized using a 1.0 molar ratio of $Cu^{2+}$ to ACA. The compounds were characterized by PXRD, IR, and SEM.

Figure 11:
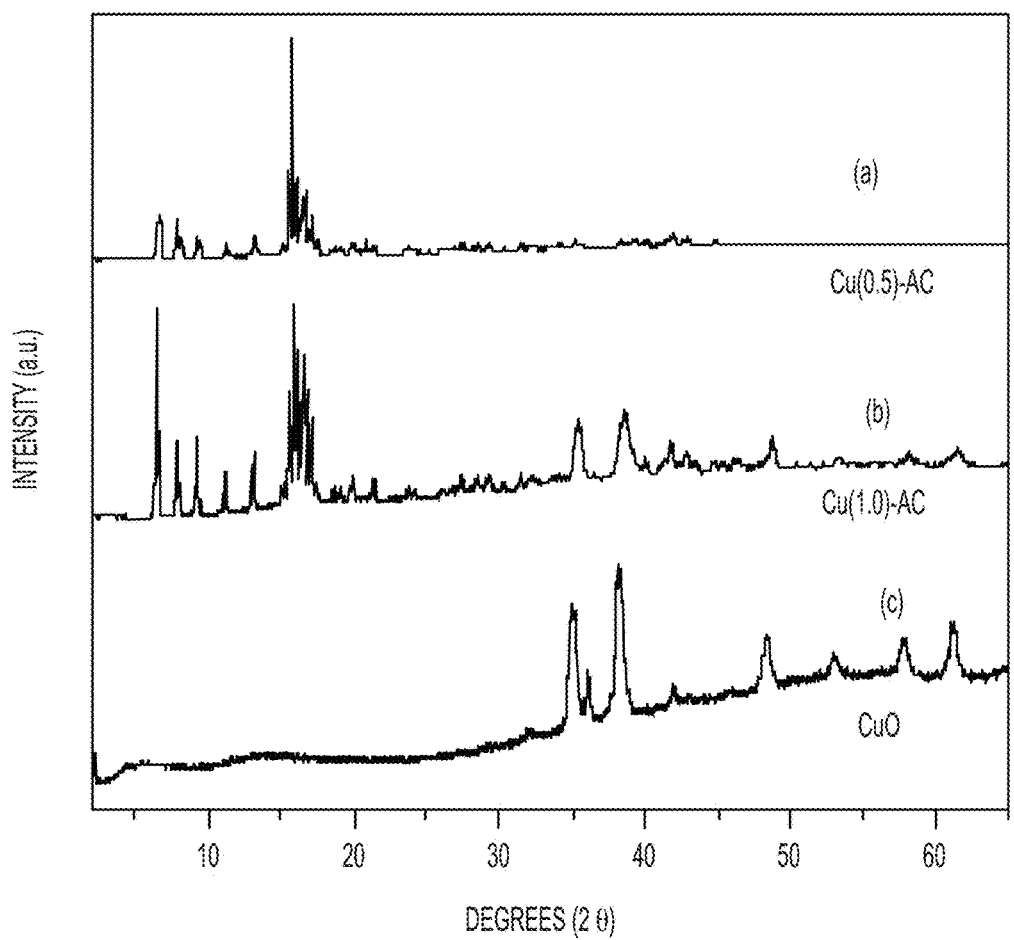
FIG. 11 shows stacked PXRD spectra of (a) a copper adamantane carboxylate compound formed from $Cu(OH)_2$ and ACA with a 0.5:1 molar ratio of $Cu^{2+}$ to ACA; (b) a copper adamantane carboxylate compound formed from $Cu(OH)_2$ and ACA with a 1.0:1 molar ratio of $Cu^{2+}$ to ACA; and (c) a copper oxide nanocomposite formed by thermally decomposing the compound of (a).

The PXRD pattern of Cu(0.5)-AC in plot (a) of FIG. 11 shows several low-angle reflections, each of which is split into multiple peaks. A first reflection exhibits peaks corresponding to d-spacings of 13.32 Å and 13.04 Å; a second reflection exhibits peaks corresponding to d-spacings of 11.25 Å, 11.11 Å, and 10.87 Å; a third reflection exhibits peaks corresponding to d-spacings of 9.46 Å and 9.26 Å; and a fourth reflection exhibits peaks corresponding to d-spacings of 7.84 Å and 7.68 Å. Higher-order reflections are present in a first group of peaks corresponding to d-spacings of 6.70 Å and 6.58 Å; in a second group of peaks corresponding to d-spacings of 5.65 Å, 5.52 Å, and 5.44 Å; and in a third group of peaks corresponding to d-spacings of 4.74 Å and 4.63 Å. These kinds of reflections in PXRD may be attributed to a compound that is: (a) layered in nature or (b) having interstratifications, that is, intergrowths of one phase with another. In addition to these reflections, Cu(0.5)-AC shows several low intensity reflections at higher 2θ values.

The IR spectrum of the Cu(0.5)-AC in plot (c) of FIG. 2 exhibits various stretching and bending vibrations. The vibrations at 2901 $cm^{-1}$ and 2844 $cm^{-1}$ arise from stretching modes of C—H bonds of adamantane ions. Symmetric and antisymmetric vibrations of $COO^-$ groups of adamantane are present at 1573 $cm^{-1}$ and 1448 $cm^{-1}$. The multiple stretching and bending modes below 1000 $cm^{-1}$ arise from metal-oxygen bonds. A broad feature at 3418 $cm^{-1}$ indicates the presence of a hydrogen-bonded hydroxyl ion in the compound. The vibration at 1659 $cm^{-1}$ is believed to arise from a bending mode of water molecules and is believed to indicate that Cu-AC has some water.

Figure 3:
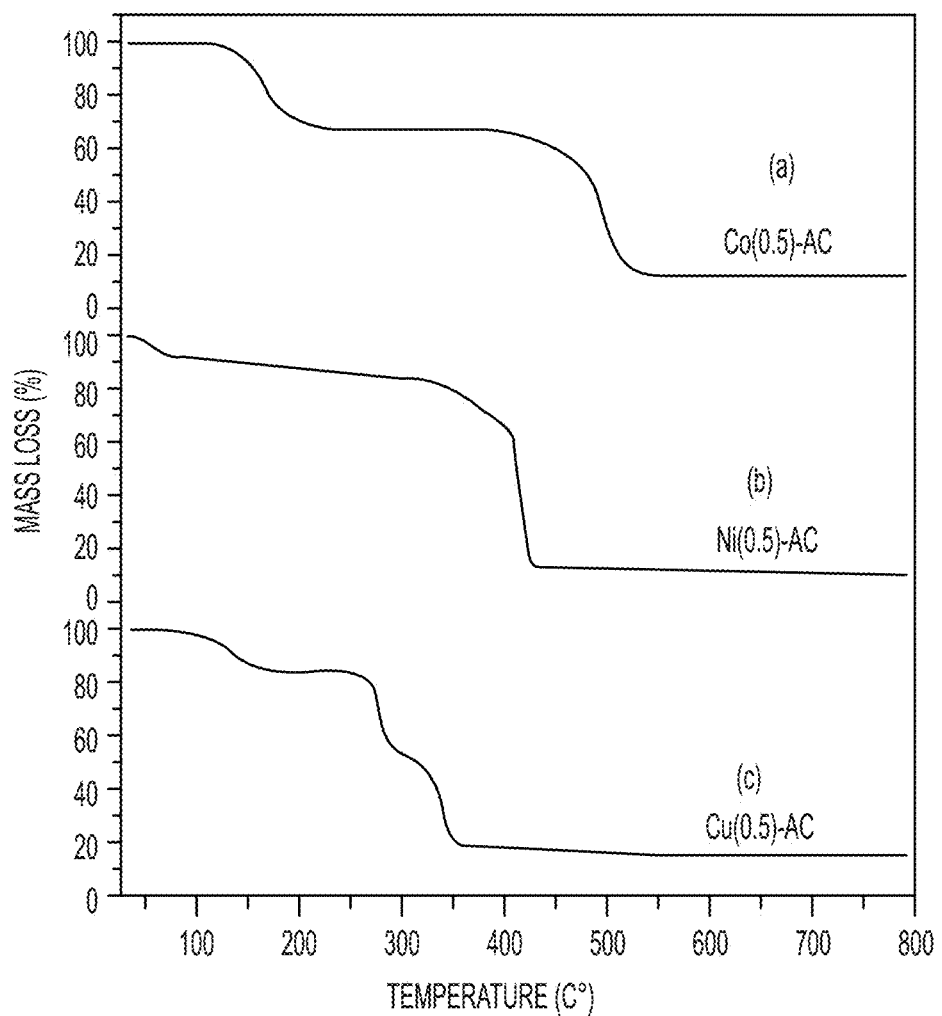
FIG. 3 includes stacked TGA profiles of adamantane carboxylate compounds formed from (a) $Co(OH)_2$ and ACA with a 0.5:1 molar ratio of $Co^{2+}$ to ACA; (b) a nickel adamantane carboxylate compound formed from $Ni(OH)_2$ and ACA with a 0.5:1 molar ratio of $Ni^{2+}$ to ACA; and (c) a copper adamantane carboxylate compound formed from $Cu(OH)_2$ and ACA with a 0.5:1 molar ratio of $Cu^{2+}$ to ACA.

In the TGA plot (c) of FIG. 3, Cu(0.5)-AC shows a three-step mass loss under air from 25° C. to 800° C. This behavior is similar to that of layered double hydroxide materials. In the TGA study, the Cu(0.5)-AC lost about 85 wt. % of its mass over the range of 25° C. to 800° C., leaving about 15 wt. % oxide residue.

Figure 12A:
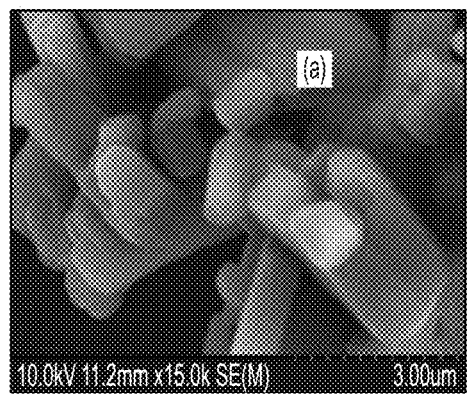
FIGS. 12A and 12B are SEM micrographs of a copper adamantane carboxylate compound formed from $Cu(OH)_2$ and ACA with a 0.5:1 molar ratio of $Cu^{2+}$ to ACA.
Figure 12B:
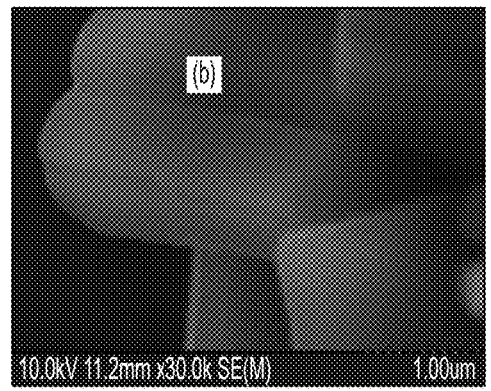

The morphology of Cu(0.5)-AC was evaluated by SEM. In the micrographs of FIGS. 12A and 12B, the Cu(0.5)-AC shows a morphology in which crystallites have grown as rectangular shapes. It is believed that the crystallite shapes indicate that Cu(0.5)-AC may have crystallized in a monoclinic crystal system.

The PXRD pattern of Cu(1.0)-AC in plot (b) of FIG. 11 is similar to the PXRD pattern of Cu(0.5)-AC in plot (a) of FIG. 11. However, a splitting of the basal reflection observed in Cu(0.5)-AC was not observed in the Cu(1.0)-AC. It is believed that the absence of the splitting of the basal reflection implies absence of interstratification in Cu(1.0)-AC. The intensities of the basal reflections were observed to be greater in the case of Cu(1.0)-AC, suggesting more ordered crystal growth.

Figure 12C:
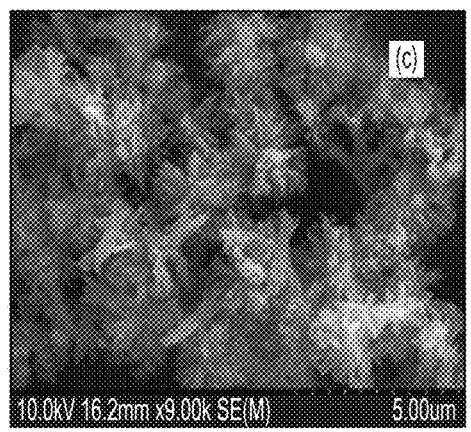
FIGS. 12C and 12D are SEM micrographs of a copper adamantane carboxylate compound formed from $Cu(OH)_2$ and ACA with a 1.0:1 molar ratio of $Cu^{2+}$ to ACA.
Figure 12D:
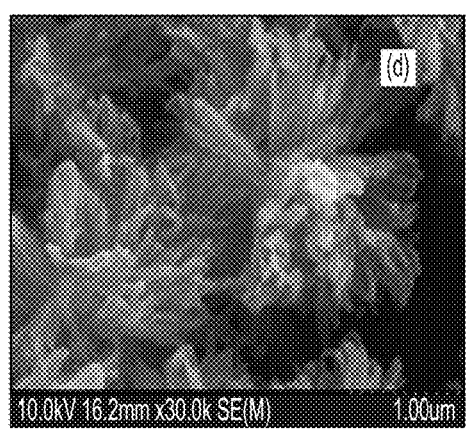
Figure 13A:
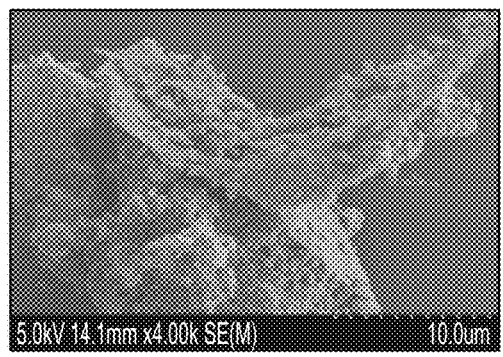
FIGS. 13A-13D are SEM micrographs of a copper oxide nanocomposite formed by thermally decomposing a copper adamantane carboxylate compound formed from $Cu(OH)_2$ and ACA with a 0.5:1 molar ratio of $Cu^{2+}$ to ACA.
Figure 13B:
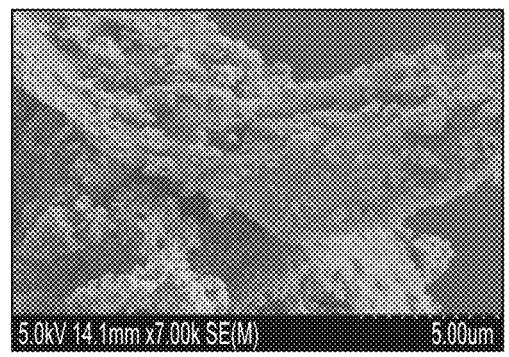
Figure 13C:
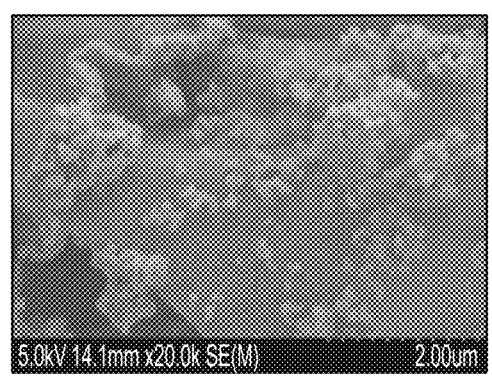
Figure 13D:
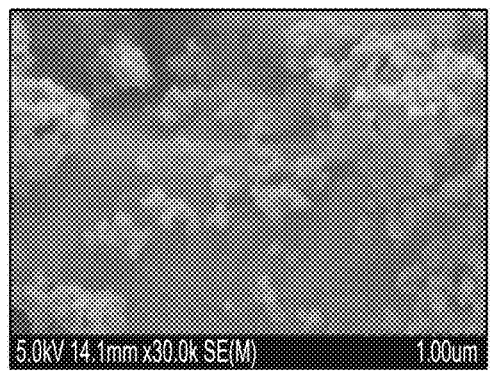

As evident from the SEM micrographs of FIGS. 12C and 12D, the Cu(1.0)-AC was observed to have a fibrous morphology, different from the rectangular crystals observed with Cu(0.5)-AC. It is believed that the lower concentration of adamantane carboxylate in Cu(1.0)-AC compared to Cu(0.5)-AC has a definite effect in facilitating higher levels of crystal growth and changes in the morphology of the Cu(1.0)-AC material.

Example 6

Copper Oxide from Thermal Decomposition of Copper Adamantane Carboxylate Salts

The Cu(0.5)-AC prepared according to Example 5 was decomposed at 450° C. for 4 h under air atmosphere. The resultant oxide material was characterized by PXRD, SEM, EDX, and TEM.

The PXRD pattern of resultant copper oxide in plot (c) of FIG. 11 exhibits reflections at 2θ angles of 29.29°, 31.95°, 35.14°, 36.11°, 38.26°, 41.96°, 43.10°, 48.35°, 53.02°, 57.81° and 61.10°, which correspond to d-spacings of 3.04 Å, 2.79 Å, 2.55 Å, 2.48 Å, 2.35 Å, 2.15 Å, 2.09 Å, 1.88 Å, 1.72 Å, 1.59 Å, and 1.51 Å, respectively. The phase identification of the resultant copper oxide revealed that majority of the copper oxide is CuO. The peaks at 2.48 Å, 2.15 Å, and 10.9 Å are attributable to $Cu_2O$, however. Thus, it is believed that resultant oxide has a mixture of both CuO and $Cu_2O$. The mixture of copper oxides may be caused by uncontrolled decomposition of the precursor Cu(0.5)-AC.

The SEM micrographs of FIGS. 13A-13D illustrate the morphology of the copper oxide obtained from the Cu(0.5)-AC. Thermal decomposition of Cu-AC compounds was expected to provide mesoporous nano-oxides of copper supported on the carbon of the adamantane carboxylate residue. As evident from the SEM micrographs of FIGS. 13A and 13B, the CuO included fine crystallites in the nanometer range that were distributed on the large sheets having lengths of greater than 10 μm. The intercalated adamantane carboxylate on decomposition grew as large sheets of carbon, on which copper oxides crystallites formed. The copper oxide crystallites are particularly evident in the SEM close-up micrographs of FIGS. 13C and 13D.

The nature and composition of the sheets and finer crystallites in the CuO was further characterized by EDX. EDX scans were conducted on areas of the large sheets and of the finer crystallites in the decomposed sample. By EDX, the sheet-like portion of the thermally decomposed Cu(0.5)-AC was observed to have a percentage of carbon atoms that was much greater than that of Cu and O atoms. The EDX spectrum of finer crystallites of the thermally decomposed Cu(0.5)-AC exhibited an amount of Cu and O substantially greater than that of carbon. The EDX spectra of both the sheet-like portion and the crystallites indicated the presence of significant amount of carbon. The distribution of the carbon in the sample was further characterized by elemental mapping. In the elemental mapping, the residual carbon was found to be distributed homogeneously throughout the sample.

Figure 14A:
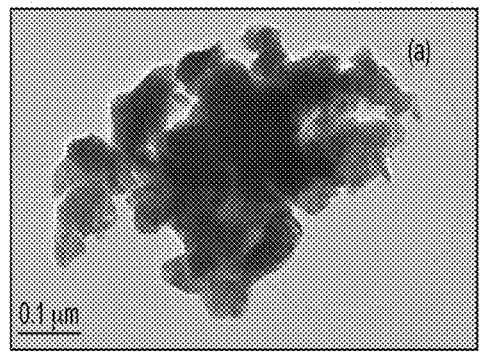
FIGS. 14A and 14B are bright-field TEM micrographs of a copper oxide nanocomposite formed by thermally decomposing a copper adamantane carboxylate compound formed from $Cu(OH)_2$ and ACA with a 0.5:1 molar ratio of $Cu^{2+}$ to ACA.
Figure 14B:
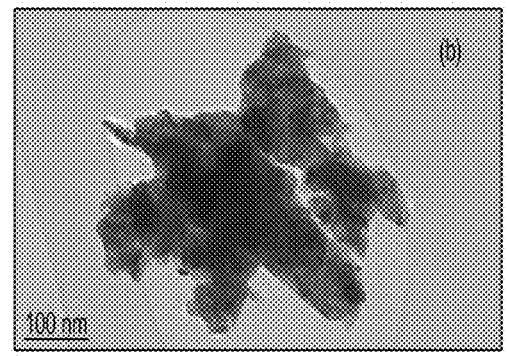
Figure 14C:
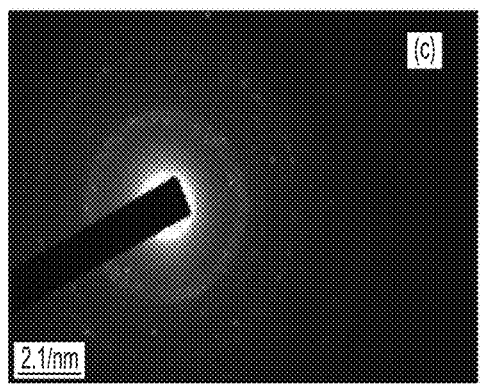
FIG. 14C is a selected-area electron diffraction pattern of the copper oxide nanocomposite of FIGS. 14A and 14B.
Figure 14D:
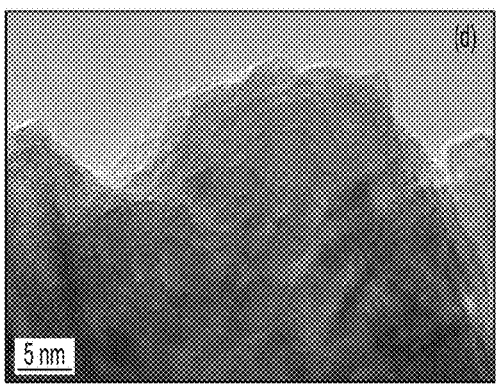
FIG. 14D is a HRTEM image of the copper oxide nanocomposite of FIGS. 14A and 14B.

The tendency of the copper oxide to grow as sheets on the carbon residue of adamantane was further confirmed by TEM images (FIGS. 14A and 14B). A selected-area electron diffraction pattern (FIG. 14C) was consistent with observations made from PXRD and SEM. The HRTEM image of the copper oxide in FIG. 14D showed lattice fringes having d-spacings matching those reported in the literature.

It should not be understood the various aspects of the composite zeolite catalyst, the method of making the same, the method of making xylene using the same, and a system for making xylene using the same are described and such aspects may be utilized in conjunction with various other aspects.

In a first aspect, the disclosure provides a method for preparing a transition-metal adamantine carboxylate salt. The method comprises mixing a transition-metal hydroxide and a diamondoid compound having at least one carboxylic acid moiety to form a reactant mixture, where M is a transition metal. The method further comprises hydrothermally treating the reactant mixture at a reaction temperature for a reaction time to form the transition-metal adamantane carboxylate salt.

In a second aspect, the disclosure provides the method of the first aspect, in which the diamondoid compound is 1-adamantane carboxylic acid and the transition metal hydroxide has the formula $M(OH)_2$, where M is chosen from Co, Cu, and Ni.

In a third aspect, the disclosure provides the method of the second aspect, in which the transition-metal hydroxide and the 1-adamantane carboxylic acid are mixed in amounts that provide a ratio of $M^{2+}$ to 1-adamantane carboxylic acid in the reaction mixture of from 0.5:1 to 1.0:1.

In a fourth aspect, the disclosure provides the method of any of the first through third aspects, in which the transition-metal hydroxide is $Co(OH)_2$ and the reaction temperature is 110° C.

In a fifth aspect, the disclosure provides the method of any of the first through third aspects, in which the transition-metal hydroxide is $Ni(OH)_2$ and the reaction temperature is 150° C.

In a sixth aspect, the disclosure provides the method of any of the first through third aspects, in which the transition-metal hydroxide is $Cu(OH)_2$ and the reaction temperature is 110° C.

In a seventh aspect, the disclosure provides the method of any of the first through sixth aspects, in which the reaction temperature is from 100° C. to 180° C.

In an eighth aspect, the disclosure provides the method of any of the first through seventh aspects, in which the reaction time is at least 12 hours.

In a ninth aspect, the disclosure provides a method for preparing a nanocomposite. The method comprises thermally decomposing a transition-metal adamantane carboxylate salt prepared according to the method of any one of the first through eighth aspects to form the nanocomposite.

In a tenth aspect, the disclosure provides the method of the ninth aspect, in which thermally decomposing the transition-metal adamantane carboxylate salt comprises heating the transition-metal adamantane carboxylate salt in air at a decomposition temperature for a decomposition time.

In an eleventh aspect, the disclosure provides the method of the tenth aspect, in which the decomposition temperature is at least 450° C.

In a twelfth aspect, the disclosure provides the method of the tenth or eleventh aspects, in which the decomposition time is at least 4 hours.

In a thirteenth aspect, the disclosure provides the method of any of the tenth through twelfth aspects, in which the nanocomposite comprises transition-metal oxide particles dispersed on a carbon support.

In a fourteenth aspect, the disclosure provides the method of the thirteenth aspect, in which the carbon support is a nanowire.

In a fifteenth aspect, the disclosure provides the method of any of the ninth through fourteenth aspects, in which the nanocomposite comprises from 70 wt. % to 80 wt. % metal oxide and from 20 wt. % to 30 wt. % carbon, based on the total weight of the nanocomposite.

In a sixteenth aspect, the disclosure provides the method of any of the ninth through fifteenth aspects, in which the transition-metal adamantane carboxylate salt comprises Co-AC.

In a seventeenth aspect, the disclosure provides the method of the sixteenth aspect, in which the nanocomposite comprises a microporous matrix and crystallites of cobalt oxide.

In an eighteenth aspect, the disclosure provides the method of the seventeenth aspect, in which the cobalt oxide comprises CoO, $Co_3O_4$, or a mixture of CoO and $Co_3O_4$.

In a nineteenth aspect, the disclosure provides the method of any of the ninth through fifteenth aspects, in which the transition-metal adamantane carboxylate salt comprises Ni-AC.

In a twentieth aspect, the disclosure provides the method of the nineteenth aspect, in which the nanocomposite comprises crystallites of NiO configured as porous nanowhiskers.

In a twenty-first aspect, the disclosure provides the method of any of the ninth through fifteenth aspects, in which the transition-metal adamantane carboxylate salt comprises Cu-AC.

In a twenty-second aspect, the disclosure provides the method of the twenty-first aspect, in which the nanocomposite comprises carbon sheets and nanoparticles of copper oxide supported on carbon sheets.

In a twenty-third aspect, the disclosure provides the method of the twenty-second aspect, in which the copper oxide comprises CuO, $Cu_2O$, or a mixture of CuO and $Cu_2O$.

In a twenty-fourth aspect, the disclosure provides a catalyst system. The catalyst system comprises (a) a transition-metal adamantane carboxylate salt prepared according to any one of the first through eighth aspects; (b) a nanocomposite prepared according to any one of the ninth through twenty-third aspects; or (c) a mixture of (a) and (b).

In a twenty-fifth aspect, the disclosure provides a method for catalyzing a chemical reaction between at least one first reactant and at least one second reactant. The method comprises reacting the at least one first reactant and at least one second reactant in the presence of a catalyst system according to the twenty-fourth aspect.

In a twenty-sixth aspect, the disclosure provides the method of the twenty-fifth aspect, in which the chemical reaction is an alcohol oxidation.

In a twenty-seventh aspect, the disclosure provides the method of the twenty-fifth aspect, in which the chemical reaction comprises a cross-coupling reaction that forms at least one carbon-nitrogen bond.

In a twenty-eighth aspect, the disclosure provides a method for catalyzing the decomposition of a reactant. The method comprises decomposing the reactant in the presence of a catalyst system according to the twenty-fourth aspect.

In a twenty-ninth aspect, the disclosure provides a polymer composite. The polymer composite comprises at least one polymer or copolymer; and at least one filler material interspersed among the at least one polymer or copolymer to form a composite. The at least one filler material is chosen from (a) a transition-metal adamantane carboxylate salt prepared according to any of the first through eighth aspects; (b) a nanocomposite prepared according to any of the ninth through twenty-third aspects; or (c) a mixture of (a) and (b).

In a thirtieth aspect, the disclosure provides a system for removing a chemical compound from a fluid stream. The system comprises an adsorbent chosen from (a) a transition-metal adamantane carboxylate salt prepared according to any of the first through eighth aspects; (b) a nanocomposite prepared according to any of the ninth through twenty-third aspects; or (c) a mixture of (a) and (b). The system also comprises a vessel in which or on which the chemical compound in the fluid stream is contacted with the adsorbent.

In a thirty-first aspect, the disclosure provides a drilling fluid. The drilling fluid comprises at least one rheology modifier chosen from (a) a transition-metal adamantane carboxylate salt prepared according to any of the first through eighth aspects; (b) a nanocomposite prepared according to any of the ninth through twenty-third aspects; or (c) a mixture of (a) and (b).

It will be apparent to those skilled in the art that various modifications and variations can be made to the embodiments described in this specification without departing from the spirit and scope of the claimed subject matter. Thus it is intended that the specification cover the modifications and variations of the various embodiments described in this specification provided such modification and variations come within the scope of the appended claims and their equivalents.

Throughout this disclosure ranges are provided. It is envisioned that each discrete value encompassed by the ranges are also included. Additionally, the ranges which may be formed by each discrete value encompassed by the explicitly disclosed ranges are equally envisioned.

What is claimed is:

1. A method for preparing a transition-metal adamantane carboxylate salt, the method comprising:
   mixing a transition-metal hydroxide and a diamondoid compound having at least one carboxylic acid moiety to form a reactant mixture, where M is a transition metal; and
   hydrothermally treating the reactant mixture at a reaction temperature for a reaction time to form the transition-metal adamantane carboxylate salt.

2. The method of claim 1, wherein the diamondoid compound is 1-adamantane carboxylic acid and the transition metal hydroxide has the formula $M(OH)_2$, where M is chosen from Co, Cu, and Ni.

3. The method of claim 2, wherein the transition-metal hydroxide and the 1-adamantane carboxylic acid are mixed in amounts that provide a ratio of $M^{2+}$ to 1-adamantane carboxylic acid in the reaction mixture of from 0.5:1 to 1.0:1.

4. The method of claim 1, wherein the transition-metal hydroxide is $Co(OH)_2$ and the reaction temperature is 110° C.

5. The method of claim 1, wherein the transition-metal hydroxide is $Ni(OH)_2$ and the reaction temperature is 150° C.

6. The method of claim 1, wherein the transition-metal hydroxide is $Cu(OH)_2$ and the reaction temperature is 110° C.

7. The method of claim 1, wherein the reaction temperature is from 100° C. to 180° C.

8. A method for preparing a nanocomposite, the method comprising:

thermally decomposing a transition-metal adamantane carboxylate salt to form the nanocomposite;
the transition-metal adamantane carboxylate salt prepared by:
mixing a transition-metal hydroxide and a diamondoid compound having at least one carboxylic acid moiety to form a reactant mixture, where M is a transition metal; and
hydrothermally treating the reactant mixture at a reaction temperature for a reaction time to form the transition-metal adamantane carboxylate salt.

9. The method of claim 8, wherein thermally decomposing the transition-metal adamantane carboxylate salt comprises heating the transition-metal adamantane carboxylate salt in air at a decomposition temperature for a decomposition time.

10. The method of claim 9, wherein the decomposition temperature is at least 450° C.

11. The method of claim 9, wherein the nanocomposite comprises transition-metal oxide particles dispersed on a carbon support.

12. The method of claim 8, wherein the nanocomposite comprises from 70 wt. % to 80 wt. % metal oxide and from 20 wt. % to 30 wt. % carbon, based on the total weight of the nanocomposite.

13. The method of claim 8, wherein the transition-metal adamantane carboxylate salt comprises Co-AC.

14. The method of claim 13, wherein the nanocomposite comprises a microporous matrix and crystallites of cobalt oxide.

15. The method of claim 8, wherein the transition-metal adamantane carboxylate salt comprises Ni-AC.

16. The method of claim 15, wherein the nanocomposite comprises crystallites of NiO configured as porous nanowhiskers.

17. The method of claim 8, wherein the transition-metal adamantane carboxylate salt comprises Cu-AC.

18. The method of claim 17, wherein the nanocomposite comprises carbon sheets and nanoparticles of copper oxide supported on carbon sheets.

19. The method of claim 18, wherein the copper oxide comprises CuO, $Cu_2O$, or a mixture of CuO and $Cu_2O$.

20. A catalyst system comprising:
(a) a transition-metal adamantane carboxylate salt prepared by:
mixing a transition-metal hydroxide and a diamondoid compound having at least one carboxylic acid moiety to form a reactant mixture, where M is a transition metal; and
hydrothermally treating the reactant mixture at a reaction temperature for a reaction time to form the transition-metal adamantane carboxylate salt;
(b) a nanocomposite prepared by:
thermally decomposing the transition-metal adamantine carboxylate salt of (a) to form the nanocomposite; or
(c) a mixture of (a) and (b).

* * * * *